(12) United States Patent
Jin et al.

(10) Patent No.: US 8,021,668 B2
(45) Date of Patent: Sep. 20, 2011

(54) INTEGRIN ALPHA L I DOMAIN MUTANTS WITH INCREASED BINDING AFFINITY

(75) Inventors: Moonsoo Jin, Ithaca, NY (US);
Timothy Springer, Chestnut Hill, MA (US)

(73) Assignee: Immune Disease Institute, Inc., Boston, MA (US)

( * ) Notice: Subject to any disclaimer, the term of this patent is extended or adjusted under 35 U.S.C. 154(b) by 152 days.

(21) Appl. No.: 12/097,004

(22) PCT Filed: Dec. 12, 2006

(86) PCT No.: PCT/US2006/047281
§ 371 (c)(1),
(2), (4) Date: Jun. 11, 2008

(87) PCT Pub. No.: WO2007/070488
PCT Pub. Date: Jun. 21, 2007

(65) Prior Publication Data
US 2008/0311130 A1    Dec. 18, 2008

Related U.S. Application Data

(60) Provisional application No. 60/749,672, filed on Dec. 12, 2005.

(51) Int. Cl.
*A61K 39/00* (2006.01)
*C07K 14/00* (2006.01)
*C07K 17/00* (2006.01)
*C07K 1/00* (2006.01)

(52) U.S. Cl. ............... 424/185.1; 514/21.2; 530/350; 530/395; 530/402

(58) Field of Classification Search ............ None
See application file for complete search history.

(56) References Cited

U.S. PATENT DOCUMENTS

| 6,120,993 | A * | 9/2000 | Ye et al. ............ 435/6 |
| 2004/0062765 | A1 | 4/2004 | Kapustay et al. |
| 2005/0182244 | A1 | 8/2005 | Springer et al. |

OTHER PUBLICATIONS

Lin et al. Directed evolution to probe protein allostery and integrin I domains of 200,000-fold higher affinity. PNAS Apr. 11, 2006 vol. 103 No. 15, pp. 5758-5763.*
Huth et al. NMR and mutagenesis evidence for an I domain allosteric site that regulates lymphocyte function-associated antigen 1 ligand binding. Proc Natl Acad Sci U S A. May 9, 2000; 97(10): 5231-5236.*
Jin et al., "Conversion Between Three Conformational States of Integrin I Domains With a C-Terminal Pull Spring Studied with Molecular Dynamics," Structure, 12:2137-2147 (2004).
Kallen et al., "Structural Basis for LFA-1 Inhibition Upon Lovastatin Binding to the CD11a I-Domain," J. Mol. Biol., 292(1):1-9 (1999).

Shimaoka et al., "Structures of the aL1 Domain and its Complex with ICAM-1 Reveal a Shape-Shifting Pathway for Integrin Regulation," Cell, 112:99-111 (2003).
Cavazzana-Calvo et al., Transplantation, 59(11):1576-1582 (1995). "Prevention of Bone Marrow and Cardiac Graft Rejection in an H-2 Haplotype Disparate Mouse Combination by an Anti-LFA-1 Antibody."
Cosimi et al., The Journal of Immunology, 144(12):4604-4612 (1990). "In Vivo Effects of Monoclonal Antibody to ICAM-1 (CD54) in Nonhuman Primates with Renal Allografts."
Cumberbatch et al., Arch Dermatol Res, 288:739-744 (1996). "Adhesion Molecule Expression by Epidermal Langerhans Cells and Lymph Node Dendritic Cells: A Comparison."
Davis et al., The Journal of Immunology, 154:3525-3537 (1995). "Induction of Persistent T Cell Hyporesponsiveness in Vivo by Monoclonal Antibody to ICAM-1 in Patients with Rheumatoid Arthritis."
Gahmberg et al., Eur. J. Biochem., 245:215-232 (1997). "Leukocyte Adhesion: Structure and Function of Human Leukocyte beta2-integrins and Their Cellular Ligands."
Hasegawa et al., International Immunology, 6(6):831-838 (1994). "Prevention of Autoimmune Insulin-Dependent Diabetes in Non-Obese Diabetic Mice by Anti-LFA-1 and Anti-ICAM-1 mAb."
Huang et al., The Journal of Biological Chemistry, 270(32):19008-19016 (1995). "A Binding Interface on the I Domain of Lymphocyte Function-Associated Antigen-1 (LFA-1) Required for Specific Interaction with Intercellular Adhesion Molecule 1 (ICAM-1)."
Isobe et al., Science, 255:1125-1127 (1992). "Scientific Acceptance of Cardiac Allograft After Treatment with Antibodies to ICAM-1 and LFA-1."
Kamata et al., The Journal of Biological Chemistry, 270(21):12531-12535 (1995). "Critical Threonine and Aspartic Acid Residues within the I Domains of beta2 Integrins for Interactions with Intercellular Adhesion Molecule 1 (ICAM-1) and C3bi."
Kavanaugh et al., Arthritis & Rheumatism, 37(7):992-999 (1994). "Treatment of Refractory Rheumatoid Arthritis with a Monoclonal Antibody to Intercellular Adhesion Molecule 1."
Kawamura et al., Circ J, 68:6-10 (2004). "Increased Expression of Monocyte CD11a and Intracellular Adhesion Molecule-1 in Patients with Initial Atherosclerotic Coronary Stenosis." Ma et al., Cellular Immunology, 158:389-399 (1994). "In Vivo Treatment with Anti-ICAM-1 and Anti-LFA-1 Antibodies Inhibits Contact Sensitization-Induced Migration of Epidermal Langerhans Cells to Regional Lymph Nodes."
Nakakura et al., Transplantation, 55(2):412-417 (1993). "Potent and Effective Prolongation by Anti-LFA-1 Monoclonal Antibody Monotherapy of Non-Primarily Vascularized Heart Allograft Survival in Mice Without T Cell Depletion."
Servitje et al., Journal of Cutaneous Pathology, 23:431-436 (1996). "Changes in T-Cell Phenotype and Adhesion Molecules Expression in Psoriatic Lesions After Low-Dose Cyclosporin Therapy."

(Continued)

Primary Examiner — Maher Haddad
(74) Attorney, Agent, or Firm — Nixon Peabody LLP

(57) ABSTRACT

The present invention provides an isolated polypeptide capable of binding to $^a$CAM-1, comprising the integrin (XL I domain or biologically active portion thereof, wherein one or more residues is substituted, wherein the substituted polypeptide binds ICAM-I at a higher affinity than wild type integrin CCL protein. The invention provides a method for inhibiting ICAM-I and a pharmaceutical composition comprising an integrin (XL I domain polypeptide or biologically active portion of the polypeptides. The invention also provides a method of treating or preventing an LFA-I mediated ICAM-1 associated disease such as inflammation, artherosclerosis, allograft rejection, diabetes, T-cell mediated sensitization reaction, psoriasis, HIV infection, or rheumatoid arthritis.

6 Claims, 4 Drawing Sheets

OTHER PUBLICATIONS

Stepkowski et al., The Journal of Immunology, 153:5336 (1994). "Blocking of Heart Allograft Rejection by Intercellular Adhesion Molecule-1 Antisense Oligonucleotides Alone or in Combination with Other Immunosuppressive Modalities."

Talento et al., Transplantation, 55(2):418-422 (1993). "A Single Administration of LFA-1 Antibody Confers Prolonged Allograft Survival."

Tibbetts et al., Transplantation, 68(5):685-692 (1999). "Peptides Derived from ICAM-1 and LFA-1 Modulate T Cell Adhesion and Immune Function in a Mixed Lymphocyte Culture."

* cited by examiner

```
130         140         150         160         170         180
NVDLVFLFDG  SMSLQPDEFQ  KILDFMKDVM  KKLSNTSYQF  AAVQFSTSYK  TEFDFSDYVK
    β1                      α1                      β2          β3    α2

190         200         210         220         230         240
WKDPDALLKH  VKHMLLLTNT  FGAINYVATE  VFREELGARP  DATKVLIIIT  DGEATDSGNI
    α3                      α4                      β4

250         260         270         280         290         300
DAAKDIIRYI  IGIGKHFQTK  ESQETLHKFA  SKPASEFVKI  LDTFEKLKDL  FTELQKKIYV
  α5    β5                  α6                      β6          α7

310
IEGTSKQDLT              SEQ. ID NO. 2
```

Figure 4

SEQUENCE LISTING

```
<160> NUMBER OF SEQ ID NOS: 4

<210> SEQ ID NO 1
<211> LENGTH: 1170
<212> TYPE: PRT
<213> ORGANISM: Homo sapiens
<220> FEATURE:
<221> NAME/KEY: SIGNAL
<222> LOCATION: (1)..(25)
<220> FEATURE:
<221> NAME/KEY: mat_peptide
<222> LOCATION: (26)..(1170)

<400> SEQUENCE: 1

Met Lys Asp Ser Cys Ile Thr Val Met Ala Met Ala Leu Leu Ser Gly
-25                 -20                 -15                 -10

Phe Phe Phe Phe Ala Pro Ala Ser Ser Tyr Asn Leu Asp Val Arg Gly
            -5                  -1  1                   5

Ala Arg Ser Phe Ser Pro Pro Arg Ala Gly Arg His Phe Gly Tyr Arg
                10                  15                  20

Val Leu Gln Val Gly Asn Gly Val Ile Val Gly Ala Pro Gly Glu Gly
                25                  30                  35

Asn Ser Thr Gly Ser Leu Tyr Gln Cys Gln Ser Gly Thr Gly His Cys
40                  45                  50                  55

Leu Pro Val Thr Leu Arg Gly Ser Asn Tyr Thr Ser Lys Tyr Leu Gly
                60                  65                  70

Met Thr Leu Ala Thr Asp Pro Thr Asp Gly Ser Ile Leu Ala Cys Asp
                75                  80                  85

Pro Gly Leu Ser Arg Thr Cys Asp Gln Asn Thr Tyr Leu Ser Gly Leu
                90                  95                  100

Cys Tyr Leu Phe Arg Gln Asn Leu Gln Gly Pro Met Leu Gln Gly Arg
            105                 110                 115

Pro Gly Phe Gln Glu Cys Ile Lys Gly Asn Val Asp Leu Val Phe Leu
120                 125                 130                 135

Phe Asp Gly Ser Met Ser Leu Gln Pro Asp Glu Phe Gln Lys Ile Leu
                140                 145                 150

Asp Phe Met Lys Asp Val Met Lys Lys Leu Ser Asn Thr Ser Tyr Gln
```

```
                155                 160                 165
Phe Ala Ala Val Gln Phe Ser Thr Ser Tyr Lys Thr Glu Phe Asp Phe
            170                 175                 180

Ser Asp Tyr Val Lys Trp Lys Asp Pro Asp Ala Leu Leu Lys His Val
185                 190                 195

Lys His Met Leu Leu Leu Thr Asn Thr Phe Gly Ala Ile Asn Tyr Val
200                 205                 210                 215

Ala Thr Glu Val Phe Arg Glu Leu Gly Ala Arg Pro Asp Ala Thr
                220                 225                 230

Lys Val Leu Ile Ile Ile Thr Asp Gly Glu Ala Thr Asp Ser Gly Asn
            235                 240                 245

Ile Asp Ala Ala Lys Asp Ile Ile Arg Tyr Ile Ile Gly Ile Gly Lys
        250                 255                 260

His Phe Gln Thr Lys Glu Ser Gln Glu Thr Leu His Lys Phe Ala Ser
    265                 270                 275

Lys Pro Ala Ser Glu Phe Val Lys Ile Leu Asp Thr Phe Glu Lys Leu
280                 285                 290                 295

Lys Asp Leu Phe Thr Glu Leu Gln Lys Lys Ile Tyr Val Ile Glu Gly
                300                 305                 310

Thr Ser Lys Gln Asp Leu Thr Ser Phe Asn Met Glu Leu Ser Ser Ser
            315                 320                 325

Gly Ile Ser Ala Asp Leu Ser Arg Gly His Ala Val Val Gly Ala Val
        330                 335                 340

Gly Ala Lys Asp Trp Ala Gly Gly Phe Leu Asp Leu Lys Ala Asp Leu
    345                 350                 355

Gln Asp Thr Phe Ile Gly Asn Glu Pro Leu Thr Pro Glu Val Arg
360                 365                 370                 375

Ala Gly Tyr Leu Gly Tyr Thr Val Thr Trp Leu Pro Ser Arg Gln Lys
                380                 385                 390

Thr Ser Leu Leu Ala Ser Gly Ala Pro Arg Tyr Gln His Met Gly Arg
            395                 400                 405

Val Leu Leu Phe Gln Glu Pro Gln Gly Gly His Trp Ser Gln Val
        410                 415                 420

Gln Thr Ile His Gly Thr Gln Ile Gly Ser Tyr Phe Gly Gly Glu Leu
    425                 430                 435

Cys Gly Val Asp Val Asp Gln Asp Gly Glu Thr Glu Leu Leu Leu Ile
440                 445                 450                 455

Gly Ala Pro Leu Phe Tyr Gly Glu Gln Arg Gly Gly Arg Val Phe Ile
                460                 465                 470

Tyr Gln Arg Arg Gln Leu Gly Phe Glu Glu Val Ser Glu Leu Gln Gly
            475                 480                 485

Asp Pro Gly Tyr Pro Leu Gly Arg Phe Gly Glu Ala Ile Thr Ala Leu
        490                 495                 500

Thr Asp Ile Asn Gly Asp Gly Leu Val Asp Val Ala Val Gly Ala Pro
    505                 510                 515

Leu Glu Glu Gln Gly Ala Val Tyr Ile Phe Asn Gly Arg His Gly Gly
520                 525                 530                 535

Leu Ser Pro Gln Pro Ser Gln Arg Ile Glu Gly Thr Gln Val Leu Ser
                540                 545                 550

Gly Ile Gln Trp Phe Gly Arg Ser Ile His Gly Val Lys Asp Leu Glu
            555                 560                 565

Gly Asp Gly Leu Ala Asp Val Ala Val Gly Ala Glu Ser Gln Met Ile
        570                 575                 580
```

-continued

```
Val Leu Ser Ser Arg Pro Val Asp Met Val Thr Leu Met Ser Phe
585                 590                 595

Ser Pro Ala Glu Ile Pro Val His Glu Val Glu Cys Ser Tyr Ser Thr
600                 605                 610                 615

Ser Asn Lys Met Lys Glu Gly Val Asn Ile Thr Ile Cys Phe Gln Ile
            620                 625                 630

Lys Ser Leu Tyr Pro Gln Phe Gln Gly Arg Leu Val Ala Asn Leu Thr
                635                 640                 645

Tyr Thr Leu Gln Leu Asp Gly His Arg Thr Arg Arg Gly Leu Phe
            650                 655                 660

Pro Gly Gly Arg His Glu Leu Arg Arg Asn Ile Ala Val Thr Thr Ser
665                 670                 675

Met Ser Cys Thr Asp Phe Ser Phe His Phe Pro Val Cys Val Gln Asp
680                 685                 690                 695

Leu Ile Ser Pro Ile Asn Val Ser Leu Asn Phe Ser Leu Trp Glu Glu
                700                 705                 710

Glu Gly Thr Pro Arg Asp Gln Arg Ala Gln Gly Lys Asp Ile Pro Pro
                715                 720                 725

Ile Leu Arg Pro Ser Leu His Ser Glu Thr Trp Glu Ile Pro Phe Glu
            730                 735                 740

Lys Asn Cys Gly Glu Asp Lys Lys Cys Glu Ala Asn Leu Arg Val Ser
745                 750                 755

Phe Ser Pro Ala Arg Ser Arg Ala Leu Arg Leu Thr Ala Phe Ala Ser
760                 765                 770                 775

Leu Ser Val Glu Leu Ser Leu Ser Asn Leu Glu Glu Asp Ala Tyr Trp
                780                 785                 790

Val Gln Leu Asp Leu His Phe Pro Pro Gly Leu Ser Phe Arg Lys Val
            795                 800                 805

Glu Met Leu Lys Pro His Ser Gln Ile Pro Val Ser Cys Glu Glu Leu
            810                 815                 820

Pro Glu Glu Ser Arg Leu Leu Ser Arg Ala Leu Ser Cys Asn Val Ser
825                 830                 835

Ser Pro Ile Phe Lys Ala Gly His Ser Val Ala Leu Gln Met Met Phe
840                 845                 850                 855

Asn Thr Leu Val Asn Ser Ser Trp Gly Asp Ser Val Glu Leu His Ala
            860                 865                 870

Asn Val Thr Cys Asn Asn Glu Asp Ser Asp Leu Leu Glu Asp Asn Ser
            875                 880                 885

Ala Thr Thr Ile Ile Pro Ile Leu Tyr Pro Ile Asn Ile Leu Ile Gln
            890                 895                 900

Asp Gln Glu Asp Ser Thr Leu Tyr Val Ser Phe Thr Pro Lys Gly Pro
905                 910                 915

Lys Ile His Gln Val Lys His Met Tyr Gln Val Arg Ile Gln Pro Ser
920                 925                 930                 935

Ile His Asp His Asn Ile Pro Thr Leu Glu Ala Val Val Gly Val Pro
            940                 945                 950

Gln Pro Pro Ser Glu Gly Pro Ile Thr His Gln Trp Ser Val Gln Met
            955                 960                 965

Glu Pro Pro Val Pro Cys His Tyr Glu Asp Leu Glu Arg Leu Pro Asp
            970                 975                 980

Ala Ala Glu Pro Cys Leu Pro Gly Ala Leu Phe Arg Cys Pro Val Val
985                 990                 995

Phe Arg Gln Glu Ile Leu Val Gln Val Ile Gly Thr Leu Glu Leu
1000                1005                1010
```

```
Val Gly Glu Ile Glu Ala Ser Ser Met Phe Ser Leu Cys Ser Ser
1015                1020                1025

Leu Ser Ile Ser Phe Asn Ser Ser Lys His Phe His Leu Tyr Gly
1030                1035                1040

Ser Asn Ala Ser Leu Ala Gln Val Val Met Lys Val Asp Val Val
1045                1050                1055

Tyr Glu Lys Gln Met Leu Tyr Leu Tyr Val Leu Ser Gly Ile Gly
1060                1065                1070

Gly Leu Leu Leu Leu Leu Leu Ile Phe Ile Val Leu Tyr Lys Val
1075                1080                1085

Gly Phe Phe Lys Arg Asn Leu Lys Glu Lys Met Glu Ala Gly Arg
1090                1095                1100

Gly Val Pro Asn Gly Ile Pro Ala Glu Asp Ser Glu Gln Leu Ala
1105                1110                1115

Ser Gly Gln Glu Ala Gly Asp Pro Gly Cys Leu Lys Pro Leu His
1120                1125                1130

Glu Lys Asp Ser Glu Ser Gly Gly Gly Lys Asp
1135                1140                1145

<210> SEQ ID NO 2
<211> LENGTH: 190
<212> TYPE: PRT
<213> ORGANISM: Homo sapiens

<400> SEQUENCE: 2

Asn Val Asp Leu Val Phe Leu Phe Asp Gly Ser Met Ser Leu Gln Pro
 1               5                  10                  15

Asp Glu Phe Gln Lys Ile Leu Asp Phe Met Lys Asp Val Met Lys Lys
            20                  25                  30

Leu Ser Asn Thr Ser Tyr Gln Phe Ala Ala Val Gln Phe Ser Thr Ser
        35                  40                  45

Tyr Lys Thr Glu Phe Asp Phe Ser Asp Tyr Val Lys Trp Lys Asp Pro
    50                  55                  60

Asp Ala Leu Leu Lys His Val Lys His Met Leu Leu Leu Thr Asn Thr
65                  70                  75                  80

Phe Gly Ala Ile Asn Tyr Val Ala Thr Glu Val Phe Arg Glu Glu Leu
                85                  90                  95

Gly Ala Arg Pro Asp Ala Thr Lys Val Leu Ile Ile Ile Thr Asp Gly
            100                 105                 110

Glu Ala Thr Asp Ser Gly Asn Ile Asp Ala Ala Lys Asp Ile Ile Arg
        115                 120                 125

Tyr Ile Ile Gly Ile Gly Lys His Phe Gln Thr Lys Glu Ser Gln Glu
    130                 135                 140

Thr Leu His Lys Phe Ala Ser Lys Pro Ala Ser Glu Phe Val Lys Ile
145                 150                 155                 160

Leu Asp Thr Phe Glu Lys Leu Lys Asp Leu Phe Thr Glu Leu Gln Lys
                165                 170                 175

Lys Ile Tyr Val Ile Glu Gly Thr Ser Lys Gln Asp Leu Thr
            180                 185                 190

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 3
ctacgctctg caggctagtg                                              20

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catctacact gttgttatca gatctcg                                      27
```

INTEGRIN ALPHA L I DOMAIN MUTANTS WITH INCREASED BINDING AFFINITY

This application is a 371 National Stage of International Application No. PCT/US2006/047281 filed on Dec. 12, 2006, which designated the U.S., and which claims the benefit under 35 U.S.C. §119(e) of U.S. Provisional Application No. 60/749,672 filed on Dec. 12, 2005, the entirety of which is incorporated herein by reference.

GOVERNMENT SUPPORT

This invention was supported, in part, by National Institutes of Health (NIH) Grants Nos. CA31798 and AI063421. The government of the United States has certain rights to the invention.

BACKGROUND OF THE INVENTION

The migration of leukocytes through the body and the various lymphoid organs is an essential element of the immune system. While circulating in blood or lymphatic vessels, leukocytes are in a resting and low adhesive state. However, when leukocytes are stimulated by signals from the immune system such as exposure to an immune complex or a chemokine gradient, their integrin adhesion receptors become activated. The activation of the integrins is essential for the many functions of leukocytes.

Such functions are, for example, binding to antigen-presenting cells, recirculation through lymph nodes and migration out of the vasculature and through the extracellular matrix to sites of inflammation. The integrin activation needs to be tightly regulated as inappropriate leukocyte adhesion leads to significant injury of normal tissues.

Leukocytes express a specific subset of the integrin family, the $\beta_2$ integrins of which four members are currently known. They have a common $\beta_2$ chain (CD 18) but different $\alpha$ subunits ($\alpha_L$/CD11a, $\alpha_M$/CD11b, $\alpha_x$/CD 11c, and $\alpha_D$/CD11d) (Gahmberg et al., 1997, Eur. J. Biochem 245:215-232). The $\alpha$ subunits contain a conserved 200-residue A or I domain, which is essential for binding of most ligands. The crystal structures of I domains from the $\alpha_L$ and $\alpha_M$ subunits indicate the presence of a cation binding site called the metal ion-dependent adhesion site (MIDAS). Amino acid substitutions in this site abrogate ligand binding (Huang and Springer, 1995, J. Biol. Chem. 270:19008-19016; Kamata et al., 1995, J. Biol. Chem. 270, 12531-12535).

The major ligands of these integrins, the ICAMs, belong to the immunoglobulin superfamily, and five ICAMs with slightly different binding specificities have been described. The expression of ICAM-1 on endothelial cells is subject to stimulation by inflammatory cytokines, which enhances the $\beta_2$ integrin-mediated adhesion of leukocytes on endothelial cells. LFA-1 dependent ICAM-1 stimulation has been implicated in leukocyte adhesion, aggregation and transendothelial migration.

Inhibition of LFA-1/ICAM-1 binding has potential therapeutic benefits relating to blocking allograft rejection, including cardiac, renal and thryoid allografts (Isobe et al., Science, 255:1125, 1992; Stepkowski et al., 1994, J Immunol., 144: 4604; Cosimi et al., 1990, J. Immunol, 144:4604; Nakakura et al., 1993, Transplantation, 55:412; Talento et al., Transplantation, 55:418, 1993), bone marrow transplants (Tibbetts et al., Transplantation, 68:685, 1999; Cavazzana-Calvo et al., Transplantation, 59:1576, 1995) T-cell mediated sensitization reactions (Ma et al., Cell Immunol., 15:389, 1994; Cumberbatch et al., Arch. Dermatol. Res., 288:739, 1996), diabetes (Hasegawa et al., Int. Immunol., 6:831, 1994), rheumatoid arthritis (Davis et al., J. Immunol., 154:3525, 1995; Kavanaugh et al., Arthritis Rheum., 37:992, 1994), and artherosclerosis (Kawamura et al. Circ J 68:6-10, 2004). Expression of ICAM-1 by keratinocytes is also implicated in the etiology of psoriasis, and inhibition of LFA-1/ICAM-1 binding presents a possible point of therapeutic intervention (Servitje et al., J. Cutan. Pathol., 23:431, 1996). Thus the peptide compositions of the present invention may be used in treatment of the above conditions and more generally in any condition T-cell mediated condition wherein T-cells are activated via interaction of LFA-1 and ICAM-1.

Because of the importance of integrins and their ligands for leukocyte function and associated diseases, antagonists of integrin-ligand binding will provide significant therapeutic benefit.

SUMMARY OF THE INVENTION

The present invention provides an isolated polypeptide capable of binding to ICAM-1, comprising the integrin $\alpha_L$ I domain or biologically active portion thereof, wherein one or more residues is substituted, wherein the substituted polypeptide binds ICAM-1 at a higher affinity than wild type integrin $\alpha_L$ protein. In one embodiment, the affinity of the isolated polypeptide to ICAM-1 is measured as having a dissociation constant ($K_D$) less than about 1500 micromolar. In one embodiment, the isolated polypeptide comprises residues 145-324 of the integrin $\alpha_L$ protein. In one embodiment, the isolated polypeptide comprises residues 129-318 of the integrin $\alpha_L$ protein. In one embodiment, the isolated polypeptide comprises residues 129-307 of the integrin $\alpha_L$ protein.

The invention provides a method for inhibiting ICAM-1, comprising administering to a subject an isolated polypeptide, comprising the integrin $\alpha_L$ I domain or biologically active portion thereof, wherein one or more residues is substituted, wherein the substituted polypeptide binds ICAM-1 at a higher affinity than wild type integrin $\alpha_L$ protein.

The invention provides a method to treat or prevent an LFA-1 mediated ICAM-1 associated disease, comprising administering to a subject in need thereof a pharmaceutical composition comprising an integrin $\alpha_L$ I domain polypeptide or biologically active portion thereof, wherein one or more residues is substituted, wherein the substituted polypeptide binds ICAM-1 at a higher affinity than wild type integrin $\alpha_L$ protein, and a pharmaceutically acceptable carrier. In one embodiment, the LFA-1 mediated ICAM-1 associated disease is inflammation, artherosclerosis, allograft rejection, diabetes, T-cell mediated sensitization reaction, psoriasis, HIV infection, or rheumatoid arthritis.

The invention provides a pharmaceutical composition comprising an integrin $\alpha_L$ I domain polypeptide or biologically active portion thereof, wherein one or more residues is substituted, wherein the substituted polypeptide binds ICAM-1 at a higher affinity than wild type integrin $\alpha_L$ protein, and a pharmaceutically acceptable carrier.

In one embodiment the substituted residues correspond to integrin $\alpha_L$ residues F134, I150, Y177, L204, F209, G246, K252, I258, G262, F265, T267, L274, F277, S279, P281, I288, L289, F292, E293, K294, L295, K296, F299, Q303, V308, I309 or any combination thereof. In one embodiment, the substituted residues are F134L, I150T, Y177R, L204Q, F209Y, G246V, K252E, I258T, G262E, F265S, F265L, T267A, L2741, F277A, F277L, S279T, P281E, I288N, I288T, L289A, L289P, L289G, L289W, F292A, F292G, F292P, F292S, E293G, K294E, L295A, L295Q, L295W, L295P, K296E, F299L, Q303R, V308I, I309T or any combination thereof.

In one embodiment, the substituted residues are I258T, T267A, and F277A.

In one embodiment, the substituted residues are F134L, K252E, and F265S.

In one embodiment, the substitutions are L274I and S279T.

In one embodiment, the substituted residues are F209Y and L289P.

In one embodiment, the substituted residues are F292S, P281E.

In one embodiment, the substituted residues are F292S, Y177R, and L204Q.

In one embodiment, the substituted residues are F265L, E293G, K294E, K296E, and V308I.

In one embodiment, the substituted residues are L295P and Q303R.

In one embodiment, the substituted residues are I150T, G246V, F299L, and I309T.

In one embodiment, the substituted residues are F277L and I288T.

In one embodiment, the substituted residues are L289, F282, L295 or any combination thereof and the substitutions are selected from the group consisting of glycine, alanine, proline and tryptophan.

In one embodiment, the substituted residues are F265S, F292A, F292G or any combination thereof.

In one embodiment, the substituted residues are F265S and F292G.

In one embodiment, the substituted residue is not F299. In one embodiment, the substituted residue is not K294C. In one embodiment, the substituted residues are not F265, L289, F292, L295, or any combination thereof.

BRIEF DESCRIPTION OF THE DRAWINGS

FIG. 3A shows inhibition of PMA-stimulated lymphocyte adhesion to ICAM-1-coated surface. Data are mean±sem from two experiments, each in triplicate. FIG. 3B shows inhibition of PMA-stimulated JY lymphoblastoid homotypic aggregation. Scoring scheme for the aggregation assay is as follows[35]: 0, no cells are in clusters; 1+, <10% of cells are in aggregates; 2+, <50% of cells are in aggregates; 3+, up to 100% of cells are in small and loose clusters; 4+, up to 100% of cells are aggregated in larger clusters; 5+, up to 100% of cells are in large, very compact clusters. Data are from two independent experiments, which showed identical results. FIG. 3C shows lymphocyte migration through endothelial monolayer. I domains were used at 1 µM, and anti-ICAM-1 antibody RR1/1 and anti-LFA-1 antibody MHM24 were at 0.33 µM. Data are mean±sem from three experiments.

FIG. 4 shows binding and switch allostery regions, and hot spots for activation in $\alpha_L$ I domain (SEQ. ID NO. 2). The wild type I domain sequence (Asn-129 to Thr-318) is shown with the secondary structure assignment: single underlines for β strands and broken underlines for α helices. All the hot spot residues where activating mutations are found are specified in bold. Binding allostery regions are found in Gly-139 to Lys-150 and in Thr-239 to Asp-246. The switch allostery region is found in Tyr-258 to Ile-310.

DETAILED DESCRIPTION OF THE INVENTION

Figure 1:
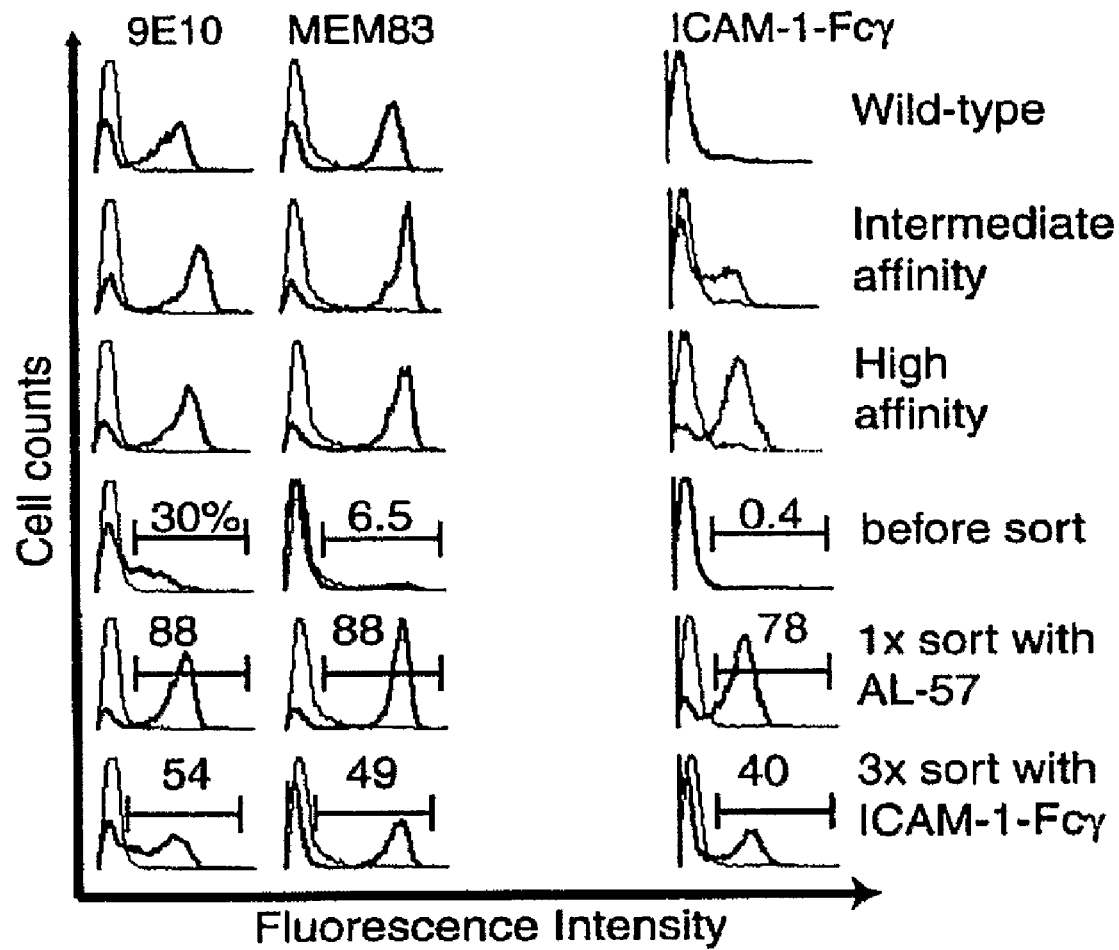
FIG. 1 shows detection of $\alpha_L$ I domains displayed on yeast cell surface by immunofluorescence flow cytometry. Cells expressing wild type, intermediate, or high affinity I domains were compared to I domains subjected to error-prone PCR. Cell surface expression was before (thin lines) and after (thick lines) induction for the binding of anti-c-myc antibody 9E10, I domain-specific antibody MEM83, and ICAM-1-Fcγ. In addition, the mutagenized I domain library was tested before and after sorting. The percentages of the cells within the gated regions are shown.

The present invention is based on the discovery that mutations in the I domain of integrin subunit $\alpha_L$ cause a striking increase in binding affinity to ICAM-1. The mutations were discovered by random mutagenesis coupled with functional screening for mutants with high affinity for ICAM-1. The mutations of the present invention are in sites that are allosteric, that is, the mutations are not located at the binding site to ICAM-1. Instead, the mutations of the present invention may change the conformation of the $\alpha_L$ I domain in order to activate binding of ICAM-1

Accordingly, the present invention provides an inhibitor of ICAM-1 binding to LFA-1, comprising a mutated $\alpha_L$ I domain peptide. The present invention further provides a therapeutic peptide for the treatment of LFA-1 dependent ICAM-1 disease, comprising a mutated $\alpha_L$ I domain peptide or biologically active portion thereof. The invention further provides a pharmaceutical composition, comprising a mutated $\alpha_L$ I domain peptide or biologically active portion thereof.

Definitions

"Integrin" and "integrin receptor" are used interchangeably herein. "Integrin" or "integrin receptor" refers to any of the many cell surface receptor proteins, also referred to as adhesion receptors which bind to extracellular matrix ligands or other cell adhesion protein ligands thereby mediating cell-cell and cell-matrix adhesion processes. Binding affinity of the integrins to their ligands is regulated by conformational changes in the integrin. Integrins are involved in physiological processes such as, for example, embryogenesis, hemostasis, wound healing, immune response and formation/maintenance of tissue architecture. The integrins are encoded by genes belonging to a gene superfamily and are typically composed of heterodimeric transmembrane glycoproteins containing non-covalently associated alpha- and beta-subunits. Integrin subfamilies contain a beta-subunit combined with different alpha-subunits to form adhesion protein receptors with different specificities.

"Lymphocyte function-associated antigen-1", "LFA-1", "$\alpha_L\beta_2$ integrin" or "CD18/CD11a" refers to a member of the leukocyte integrin subfamily. The inserted or I domain of the $\alpha_L$ subunit is an allosteric mediator of ligand binding to LFA-1. The I domain encompasses amino acid residues 145-324 of the 1145 amino acid long mature $\alpha_L$ integrin subunit protein (amino acid residues 26-1170 of GenBank Accession No. NP_002200). The ligand binding site of the I domain, known as a metal ion-dependent adhesion site (MIDAS), exists as two distinct conformations allosterically regulated by the C-terminal α7-helix. As used herein, "integrin $\alpha_L$", "$\alpha_L$ integrin", "$\alpha_L$", "CD11a", "p180", "lymphocyte function-associated antigen 1 $\alpha_L$ subunit", "ITGAL-$\alpha_L$ subunit" or "$\alpha_L$ polypeptide" in lieu of subunit are used interchangeably. Integrin $\alpha_L$ refers to the mature protein encoded by the ITGAL gene (GenBank Accession No. NM_002209). All numbering of amino acid residues as used herein refer to the amino acid sequence of the mature $\alpha_L$ integrin as found in GenBank Accession No. NP_002200, wherein residue 1 corresponds to residue 26 of NP_002200 (SEQ ID NO: 1).

"Intercellular adhesion molecule-1" or "ICAM-1", i.e. GenBank Accession Nos. NM_000201, NP_000192, is the ligand for $\alpha_L\beta_2$ integrin, and its N-terminal domain (D1) binds to the $\alpha_L$ I domain through the coordination of ICAM-1 residue Glu-34 to the MIDAS metal. ICAM-1 is exploited by Rhinovirus as a receptor (Greve et al. Cell 1989; 56: 839-847) and is implicated in HIV infection (Swingler et al. Nature 2003; 424: 213-219). ICAM1 is typically expressed on endothelial cells and cells of the immune system. ICAM1 binds to integrins of type $\alpha_L\beta_2$ and $\alpha_M\beta_2$.

"Peptide", "polypeptide" and "protein" are used interchangeably herein. "Peptide" and "polypeptide" refer to any chain of amino acids, regardless of length or post-translational modification (e.g., glycosylation or phosphorylation).

As used herein, "treatment" or "treating a patient" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, palliate, improve or affect the disease, the symptoms of disease or the predisposition toward disease. A therapeutic agent includes, but is not limited to, small molecules, peptides, antibodies, ribozymes and antisense oligonucleotides. "Treatment" or "treating a patient" refer to both therapeutic treatment and prophylactic or preventative measures. Those in need of treatment include those already with the disorder as well as those in which the disorder is to be prevented.

As used herein, an "isolated" or "purified" polypeptide or protein, or biologically active portion thereof is substantially free of cellular material or other contaminating proteins from the source, e.g., the cellular source, from which the integrin $\alpha_L$ I-domain polypeptide is derived, or substantially free from chemical precursors or other chemicals when chemically synthesized. The language "substantially free of cellular material" includes preparations of integrin $\alpha_L$ I-domain polypeptide in which the protein is separated from cellular components of the cells from which it is isolated or recombinantly produced. In one embodiment, the language "substantially free of cellular material" includes preparations of integrin $\alpha_L$ I domain polypeptide having less than about 30% (by dry weight) of wild type integrin $\alpha_L$ polypeptide (also referred to herein as a "contaminating protein"), more preferably less than about 20% of wild type integrin $\alpha_L$ polypeptide, still more preferably less than about 10% of wild type integrin $\alpha_L$ polypeptide, and most preferably less than about 5% wild type integrin $\alpha_L$ polypeptide. When the integrin $\alpha_L$ I-domain polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

As used herein, the language "substantially free of chemical precursors or other chemicals" includes preparations of integrin $\alpha_L$ I-domain polypeptide in which the protein is separated from chemical precursors or other chemicals which are involved in the synthesis of the protein. In one embodiment, the language "substantially free of chemical precursors or other chemicals" includes preparations of integrin $\alpha_L$ I-domain polypeptide having less than about 30% (by dry weight) of chemical precursors or wild type integrin $\alpha_L$ polypeptide chemicals, more preferably less than about 20% chemical precursors or wild type integrin $\alpha_L$ polypeptide chemicals, still more preferably less than about 10% chemical precursors or wild type integrin $\alpha_L$ polypeptide chemicals, and most preferably less than about 5% chemical precursors or wild type integrin $\alpha_L$ polypeptide chemicals.

As used herein, a "biologically active portion" or "biologically active fragment" of an $\alpha_L$ integrin polypeptide, e.g. an integrin $\alpha_L$ I-domain polypeptide, includes a fragment of an integrin $\alpha_L$ polypeptide which retains an integrin $\alpha_L$ polypeptide activity, e.g. binding affinity to ICAM-1, including increased binding affinity relative to wild type. Typically, a biologically active portion of an integrin $\alpha_L$ polypeptide comprises at least one domain or motif with at least one activity of the integrin $\alpha_L$ polypeptide, e.g., ligand binding. In a preferred embodiment, biologically active portions of an integrin $\alpha_L$ polypeptide include integrin $\alpha_L$ I-domain polypeptides. Biologically active portions of a integrin $\alpha_L$ polypeptide may comprise amino acid sequences sufficiently identical to or derived from the amino acid sequence of an $\alpha_L$ integrin polypeptide, which include fewer amino acids than the full length integrin $\alpha_L$ polypeptide, and exhibit at least one activity of an integrin $\alpha_L$ polypeptide, e.g. binding affinity for ICAM-1. Biologically active portions of an integrin $\alpha_L$ polypeptide, e.g., an I-domain or I-like domain, can be used as targets for developing agents which modulate a integrin $\alpha_L$ polypeptide activity, e.g., ligand binding, adhesion, e.g., cell to cell adhesion or cell to extracellular matrix adhesion, and/or signaling activity. Biologically active portions of an integrin $\alpha_L$ polypeptide, e.g., an I-domain or I-like domain, can be used as inhibitors of ICAM-1, e.g. therapeutic agents to treat or prevent ICAM-1 associated disease or condition. Preferably, the ICAM-1 associated disease or condition is LFA-1 dependent. A biologically active portion of an integrin $\alpha_L$ polypeptide comprises a polypeptide which can be prepared by recombinant techniques and evaluated for one or more of the functional activities of an integrin $\alpha_L$ polypeptide.

As used herein, the term "sufficiently identical" refers to an amino acid (or nucleotide) sequence which contains a sufficient or minimum number of identical or equivalent (e.g., an amino acid residue that has a similar side chain) amino acid residues (or nucleotides) to a integrin amino acid (or nucleotide) sequence such that the polypeptide shares common structural domains or motifs, and/or a common functional activity with a native integrin polypeptide. For example, amino acid or nucleotide sequences which share at least about 30%, about 40%, or about 50%, preferably about 60%, more preferably about 70%, about 75%, about 80%, about 85% or about 90%, about 91%, about 92%, about 93%, about 94%, about 95% or greater identity and share a common functional activity (e.g., an activity of an integrin $\alpha_L$ I-domain, e.g., binding affinity to ICAM-1 as described herein) are defined herein as sufficiently identical. An integrin $\alpha_L$ I-domain polypeptide may differ in amino acid sequence from the integrin polypeptides disclosed herein due to natural allelic variation or mutagenesis.

To determine the percent identity of two amino acid sequences or of two nucleic acid sequences, the sequences are aligned for optimal comparison purposes, e.g., gaps can be introduced in one or both of a first and a second amino acid or nucleic acid sequence for optimal alignment and non-identical sequences can be disregarded for comparison purposes. In a preferred embodiment, the length of a reference sequence aligned for comparison purposes is at least about 30%, preferably at least about 40%, more preferably at least about 50%, even more preferably at least about 60%, and even more preferably at least about 70%, about 80%, or about 90% of the length of the reference sequence, e.g. GenBank Accession No. NP_002200. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (Accelrys Software Inc.), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al, Nucleic Acids Res. 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4.

Allosteric Activation of I Domains

Within many signaling proteins, conformational changes from inactive to active states can be induced by allostery[1]. In the inserted (I) domain, a single modular domain present in some integrin α subunits, allosteric activation pathways have been studied structurally and functionally[2-10]. The ligand binding site of the I domain, known as a metal ion-dependent adhesion site (MIDAS), exists as two distinct conformations allosterically regulated by the C-terminal α7-helix (Jin et. al. 2006 PNAS 103: 5758-63). Intercellular adhesion molecule-1 (ICAM-1) is the ligand for $α_Lβ_2$ integrin. The N-terminal domain (D1) of ICAM-1 binds to the $α_L$ I domain through an interface that buries 1250 Å; at the center of this interface ICAM-1 residue Glu-34 coordinates to the MIDAS metal (Jin et. al. 2006 PNAS 103: 5758-63).

The existence of allosteric activation in I domains was first suggested from structural studies of I domains that were crystallized in two conformations termed closed and open; subsequent mutational studies and co-crystallization with ligands demonstrated that closed and open conformations have low and high affinity for ligand, respectively[6, 9-14]. Remarkable differences between the two conformations were found in the MIDAS and the position of the α7-helix (Jin et. al. 2006 PNAS 103: 5758-63), which exhibits axial C-terminal or "downward" displacement of 10 Å in the open conformation. In an intact integrin, interaction of the linker region following the α7-helix with the neighboring I-like domain of the β subunit exerts the force that pulls the α7-helix downward[3, 15, 16].

Experts using structural insight have designed mutations to study allostery in α I domains. In the $α_M$ I domain, two buried hydrophobic residues (Phe-275 and Phe-302) become more exposed to solvent as the I domain shifts from closed to open conformation. The mutations F275R and F302W led to a 2-fold increase in cell adhesion[2]. The allosteric role of the α7-helix was more directly demonstrated in the $α_L$ I domain. Pairs of cysteines were introduced in the $α_L$ I domain to stabilize the α7-helix in intermediate or open positions, and this led, respectively, to 500 and 10,000-fold higher affinity to ICAM-1 than the wild-type I domain, which exists with its α7-helix predominantly in the closed position[5, 6]. Stabilizing the α7-helix of the $α_M$ I domain in the open conformation with disulfide bonds also substantially increased affinity[7, 17]. Furthermore, mutation to Gly of an Ile in the α7-helix that inserts into a hydrophobic pocket in the closed position of the α7-helix (I317G in $α_M$ and I306G in $α_L$) led to an increase in affinity for ligands[3, 18].

In addition to the success of expert design in creating active I domain mutants, computational design was used to generate high affinity mutants of the $α_M$ I domain[19]. Mutations in the hydrophobic core of the $α_M$ I domain were found by computationally searching for substitutions that would stabilize the open structure. Most of the predicted active mutants were expressed and had higher affinity for ligand than wild type.

Alpha L Integrin I Domain Polypeptides

The peptides of the present invention comprise mutants of the $\alpha_L$ integrin I domain that bind to ICAM-1 with an affinity greater than the wild type $\alpha_L$ integrin I domain. The peptides may comprise biologically active portions of the $\alpha_L$ integrin I domain wherein the peptide binds to ICAM-1 with an affinity greater than the wild type. In one embodiment, the peptides comprise the full length $\alpha_L$ integrin. In one embodiment, the peptides comprise amino acid residues 129 to 318 of $\alpha_L$ integrin. All numbering of amino acid residues as used herein refer to amino acid sequence of native $\alpha_L$ integrin as found in GenBank Accession No. NP_002200. Mutations in the $\alpha_L$ integrin I domain wherein binding affinity to ICAM-1 is increased are listed in Table 1.

In one embodiment, the peptides of the present invention have substitution mutations in residues F134, I150, Y177, L204, F209, G246, K252, I258, G262, F265, T267, L274, F277, S279, P281, I288, L289, F292, E293, K294, L295, K296, F299, Q303, V308, I309 or any combination thereof. In one embodiment, the peptides have $\alpha_L$ integrin substitution mutations including F134L, I150T, Y177R, L204Q, F209Y, G246V, K252E, I258T, G262E, F265S, F265L, T267A, L274I, F277A, F277L, S279T, P281E, I288N, I288T, L289A, L289P, L289G, L289W, F292A, F292G, F292P, F292S, E293G, K294E, L295A, L295Q, L295W, L295P, K296E, F299L, Q303R, V308I, I309T or any combination thereof.

In one embodiment, the substitutions are I258T, T267A, and F277A. In one embodiment, the substitutions are F134L, K252E, and F265S. In one embodiment, the substitutions are L274I and S279T. In one embodiment, the substitutions are F209Y and L289P. In one embodiment, the substitutions are F292S, P281E. In one embodiment, the substitutions are F292S, Y177R, and L204Q. In one embodiment, the substitutions are F265L, E293G, K294E, K296E, and V308I. In one embodiment, the substitutions are L295P and Q303R. In one embodiment, the substitutions are I150T, G246V, F299L, and I309T. In one embodiment, the substitutions are F277L and I288T.

In one embodiment, L289 is substituted with glycine, alanine, proline or tryptophan. In one embodiment, F292 is substituted with glycine, alanine, proline or tryptophan. In one embodiment, L295 is substituted with glycine, alanine, proline or tryptophan. In one preferred embodiment, the substitutions are F265S, F292A, F292G or any combination thereof. In one preferred embodiment, the substitutions are F265S and F292G.

In one embodiment, F299 is not mutated. In one embodiment, K294 is not substituted with cysteine. In one embodiment, F299 is not substituted with cysteine. In one embodiment I306, I330, and I331 are not mutated. In one embodiment, F265, L289, F292, L295, or any combination thereof are not mutated.

Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Conservative substitutions replace a residue with another that is a member of the same group. Non-conservative substitutions entail exchanging a member of one of these classes for a member of another class. In one embodiment, the substitutions in the residues of the I domain peptides of the present invention are non-conservative substitutions.

Isolated integrin $\alpha_L$ I domain polypeptides of the present invention preferably have an amino acid sequence that is sufficiently identical to the amino acid sequence of a native or wild type integrin $\alpha_L$ polypeptide, yet which comprise at least one, alternatively two, alternatively more than two, substitutions in the I domain, such that binding affinity to ICAM-1 is increased relative to the native protein. Isolated integrin $\alpha_L$ I domain polypeptides of the present invention may comprise a biologically active portion of the wildtype integrin $\alpha_L$ I domain.

The $\alpha_L$ integrin I domain polypeptide, or biologically active fragment thereof, of the present invention may be based on the $\alpha_L$ integrin protein from any number of organisms, with $\alpha_L$ integrin proteins from mammals being particularly preferred. Suitable mammals include, but are not limited to, rodents (rats, mice, hamsters, guinea pigs, etc.), primates, farm animals (including sheep, goats, pigs, cows, horses, etc) and in the most preferred embodiment, from humans. As will be appreciated by those in the art, the polypeptides of the present invention based on $\alpha_L$ integrin proteins from mammals other than humans may find use in animal models of human disease.

A polypeptide of this invention may be an expression product of a mutated ITGAL gene, a mutated I domain of the ITGAL gene or fragment thereof. These peptides may be prepared by methods involving isolating peptides from the cells transformed by an expression vector containing the mutated ITGAL gene, mutated I domain of the ITGAL gene or fragment thereof. Cells for transformation may include prokaryotic or eukaryotic, including yeast, insect, or mammalian. Methods of chemical synthesis on the basis of a desired amino acid sequence of the mutations of the present invention and by production and isolation or purification from the above-mentioned transformed cells are known to the skilled artisan. Such transformed cells are incubated and isolation and purification are carried out for the culture by, for example, means of treatment with a modifier such as urea or with a surface-active agent, ultrasonic wave treatment, enzymatic digestion, precipitation by salting out or by solvent, dialysis, centrifugal separation, ultrafiltration, gel filtration, SDS-PAGE, isoelectric electrophoresis, ion exchange chromatography, hydrophobic chromatography, affinity chromatography and reversed phase chromatography. Such proteins may include fused proteins with any other protein. For example, fused proteins with glutathione-S-transferase (GST) or green fluorescent protein (GFP) may be exemplified. In addition, the protein expressed in cells may be subjected to various kinds of modifications in the cells after being translated. Accordingly, modified proteins are also included in the coverage of the protein of this invention. Examples of the modification after translation as such are elimination of N-terminal methionine, N-terminal acetylation, addition of sugar chain, limited decomposition by intracellular protease, myristoylation, isoprenylation and phosphorylation.

The polypeptides of the present invention prepared as described above may be subjected to further modifications, oftentimes depending on the intended use of the polypeptide. Such modifications may involve further alteration of the amino acid sequence, e.g. substitution, insertion and/or deletion of amino acid residues, fusion to heterologous polypeptide(s), such as epitope tags, immunoglobulins or regions of immunoglobulins, and/or covalent modifications, e.g. linking to nonproteinacious polymers. Such "further modifications" may be made prior to, simultaneously with, or following, the amino acid modification(s) disclosed above which result in an alteration of binding affinity of the I domain with ICAM-1.

With respect to further amino acid sequence alterations, any cysteine residue not involved in maintaining the proper conformation of the polypeptide of the present invention, e.g. the integrin $\alpha_L$ I domain polypeptide, also may be substituted, generally with serine, to improve the oxidative stability of the molecule and prevent aberrant cross linking.

Another type of amino acid substitution serves to alter the glycosylation pattern of the polypeptide. This may be achieved by deleting one or more carbohydrate moieties found in the polypeptide, and/or adding one or more glycosylation sites that are not present in the polypeptide. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original polypeptide (for O-linked glycosylation sites). Chemical deglycosylation may be performed.

In one embodiment, the peptides of the present invention may include peptidomimetic or peptoid residues or segments. Peptidomimetics are chemical variants of a polypeptide or a peptide in which the side chains of the polypeptide or peptide are substantially maintained in the variant, yet the chemical backbone of the peptidomimetic is altered relative to the polypeptide or peptide in at least one peptide bond. A peptoid is an oligomer of N-substituted glycines. A peptoid can be synthesized from a variety of different N-alkylglycines that have side chains similar to amino acid side chains, (e.g., as described in Simon et al., (1992) PNAS 89:9367-9371). It can serve as a motif for the generation of chemically diverse libraries of novel molecules. As an alternative to natural polymers, it is a modular system that allows one to synthesize monomers in large amounts. The monomers have a wide variety of functional groups presented as side chains off of an oligomeric backbone, the linking chemistry is high yielding and amenable to automation. The linkage in a peptoid is resistant to hydrolytic enzymes such as proteases. Another advantage is that the monomers are achiral.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation although substituted with a sidechain of similar conformation. Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Thus, for example, it may be possible to change only a few (or one) residues, or most of the residues, with all possibilities in between.

In a preferred embodiment, residues which can be fixed include, but are not limited to, structurally or biologically functional residues; alternatively, biologically functional residues may specifically not be fixed. For example, residues which are known to be important for biological activity, such as the residues which the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in a conformation.

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable enzyme activity but with a preservation of binding, etc.

Alpha L Integrin I Domain Polypeptide Production

For recombinant production of the polypeptide, e.g. integrin $\alpha_L$ I domain polypeptide, the nucleic acid encoding it is isolated and inserted into a replicable vector for further cloning (amplification of the DNA) or for expression. DNA molecules encoding all or part of $\alpha_L$ integrin can be readily obtained by means of conventional procedures, e.g. polymerase chain reaction amplification (PCR). In this technique two short DNA primers are used to generate multiple copies of a DNA fragment of interest from cells known to harbor the mRNA produced by the gene of interest or from cDNA. This technique is described in detail by Frohman et al., Proc. Nat'l Acad Sci. USA 85:8998 (1988). Polymerase chain reaction methods are generally described by Mullis et al. (U.S. Pat. Nos. 4,683,195 and 4,683,202). Alternatively, an $\alpha_L$ integrin cDNA clone, full-length or partial, containing the I domain may be used. cDNA clones may be obtained commercially, e.g. clones from the I.M.A.G.E. clone database available from Invitrogen Corp., Carlsbad Calif., or isolated from a cDNA library. The entire cDNA clone may be used for expression or a fragment, e.g. the I domain, may be used for expression. Fragments of a cDNA clone may be isolated by means of restriction digest.

The substitution mutation of interest may be engineered into the DNA molecule encoding the $\alpha_L$ I domain polypeptide by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Site-directed mutagenesis is a preferred method for preparing substitution mutations. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants, e.g. substitution mutations, of the starting polypeptide, e.g. integrin $\alpha_L$. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, e.g. substitutions, is cassette mutagenesis, based on the technique described by Wells et al., Gene 34:315-323 (1985). The starting material is the plasmid (or other vector) comprising the starting polypeptide DNA, e.g. integrin $\alpha_L$ I domain, to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a polypeptide substitution mutant or variant, e.g. the integrin $\alpha_L$ I domain polypeptide, can be determined, and a nucleic acid sequence encoding such amino acid sequence variant can be generated synthetically.

Many vectors, e.g. expression vectors, are available. The vector components generally include, but are not limited to, one or more of the following: a signal sequence, an origin of replication, one or more marker genes, an enhancer element, a promoter, and a transcription termination sequence.

(i) Signal Sequence Component

The polypeptide of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native polypeptide signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, .alpha. factor leader (including Saccharomyces and Kluyveromyces α-factor leaders), or acid phosphatase leader, the C. albicans glucoamylase leader, or the signal described in WO 90/13646. In mammalian cell expression, mammalian signal sequences as well as viral secretory leaders, for example, the Herpes Simplex gD signal, are available. The DNA for such precursor region is ligated in reading frame to DNA encoding the polypeptide of the present invention.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2.mu. plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the polypeptide nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding the polypeptide, e.g. sequences encoding integrin $\alpha_L$ I domain, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of Kluyveromyces yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968-975 (1991).

(iv) Promoter Component

Expression and cloning vectors usually contain a promoter that is recognized by the host organism and is operably linked to the polypeptide nucleic acid, e.g. integrin $\alpha_L$ I domain nucleic acid. Promoters-suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide, e.g. integrin $\alpha_L$ I domain.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription of the polypeptide, e.g. integrin $\alpha_L$ I domain, from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human .beta.-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide, e.g. integrin $\alpha_L$ I domain polypeptide. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, *Enterobacteriaceae* such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells ($CV_1$ ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

(viii) Culturing the Host Cells

The host cells used to produce the polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195, or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Polypeptide Purification

When using recombinant techniques, the polypeptide can be produced intracellularly, in the periplasmic space, or directly secreted into the medium. If the polypeptide is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The polypeptide composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the polypeptide. Protein A can be used to purify polypeptides that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the polypeptide comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ (gel filtration substance; Pharmacia Inc., Piscataway, N.J.) chromatography on an anion or cation exchange resin (such as a polyaspartic acid column), chromatofocusing, SDS-PAGE, and ammonium sulfate precipitation are also available depending on the polypeptide to be recovered.

Following any preliminary purification step(s), the mixture comprising the polypeptide of interest and contaminants may be subjected to low pH hydrophobic interaction chromatography using an elution buffer at a pH between about 2.5-4.5, preferably performed at low salt concentrations (e.g., from about 0-0.25M salt).

Affinity of the Alpha L Integrin Polypeptide for ICAM-1

The integrin $\alpha_L$ I domain polypeptide of the present invention may be assayed for its binding affinity for ICAM-1 by methods known to the skilled artisan. Both in vivo and in vitro assays may be used for experimental testing and validation. Suitable assays include, but are not limited to, e.g., examining their binding affinity to natural occurring or variant full-length or partial ICAM-1 polypeptides or to I domain specific antibodies. In addition to cell-free biochemical affinity tests, quantitative comparison are made comparing kinetic and equilibrium binding constants for the ligands to the naturally occurring integrin $\alpha_L$ and to the integrin $\alpha_L$ I domain proteins of the present invention. The kinetic association rate ($K_{on}$) and dissociation rate ($K_{off}$), and the equilibrium binding constants ($K_d$) can be determined using surface plasmon resonance on a BIAcore instrument following the standard procedure in the literature [Pearce et al., Biochemistry 38:81-89 (1999)]. Comparing the binding constant between a natural integrin $\alpha_L$ and its corresponding naturally occurring target, e.g. ICAM-1, with the binding constant of a integrin $\alpha_L$ I domain protein of the present invention is made in order to evaluate the sensitivity and specificity of the integrin $\alpha_L$ protein to its natural target molecule. Preferably, binding affinity of the integrin $\alpha_L$ I domain protein of the present invention, e.g. to natural targets, e.g. to ICAM-1, increases relative to the naturally occurring integrin $\alpha_L$.

In one embodiment, an integrin α L I domain polypeptides can be used as a ICAM-1 targeting molecule to activated endothelial cells for a variety of purposes, including, for example: Specific targeting for therapeutic delivery to vascular endothelial cells (EC), more specifically to cells that express ICAM-1, for example human bronchial epithelial cells, pulmonary endothelial cells, human umbilical vein endothelial cells (HUVEC), and osteoblasts. Therapeutics can be in the form of chemical drug formulation, anti-sense oligonucleotides, siRNA, and radioisotopes. Therapeutics can be encapsulated in glycol-lipsomes or in nanoparticles Specific targeting to endothetial cells for enhanced imaging of EC tissue during disease progression and treatment regime. For example, magnetic resonance contrast agent such as paramagnetic liposomes when conjugated to integrin α L I domain polypeptides can be use to visualize cerebral microvasculature in autoimmune encephalitis by magnetic resonance imaging (J. Neuronimmunol. 2000, 104:1-9). Atherosclerotic plagues can be monitored by acoustic (ultrasomic) imaging using liposomes conjugates (J. Am. Coll. Cardiol. 1999, 33:867-75). Antibodies to Integrin Alpha L I Domain Polypeptides An isolated integrin $\alpha_L$ polypeptide, e.g., a $\alpha_L$ I domain polypeptide, or a biologically active portion or fragment thereof, can be used as an immunogen to generate antibodies that bind to a specific conformation of an integrin $\alpha_L$ protein, e.g., an integrin $\alpha_L$ I-domain, using standard techniques for polyclonal and monoclonal antibody preparation (see, generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet. 3:231-36). Moreover, the ordinarily skilled artisan will appreciate that there are many variations of such methods which also would be useful. Preparation of anti-integrin $\alpha_L$ antibodies is described in, for example, U.S. Pat. No. 5,622,700, the entire content of which is incorporated herein by this reference.

The term "antibody" as used herein refers to immunoglobulin molecules and immunologically active portions of immunoglobulin molecules, i.e., molecules that contain an antigen binding site, e.g. an antigen binding fragment, which specifically binds (immunoreacts with) an antigen, e.g., an integrin $\alpha_L$ I-domain polypeptide of the present invention, e.g., an integrin $\alpha_L$ I-domain in an open conformation. Examples of immunologically active portions of immunoglobulin molecules include F(ab) and F(ab')$_2$ fragments which can be generated, for example, by treating the antibody with an enzyme such as pepsin. The invention provides polyclonal and monoclonal antibodies that bind to the integrin $\alpha_L$ polypeptide of the present invention or to a portion or fragment thereof. The term "monoclonal antibody" or "monoclonal antibody composition", as used herein, refers to a population of antibody molecules that contain only one species of an antigen binding site capable of immunoreacting with a particular epitope of a modified integrin $\alpha_L$ polypeptide, e.g., a integrin $\alpha_L$ I domain polypeptide, or a portion or fragment thereof. A monoclonal antibody composition thus typically displays a single binding affinity for a particular integrin $\alpha_L$ polypeptide of the present invention, or a portion or fragment thereof with which it immunoreacts.

Alternative to preparing monoclonal antibody-secreting hybridomas, a monoclonal anti-integrin antibody can be identified and isolated by screening a recombinant combinatorial immunoglobulin library (e.g., an antibody phage display library) with an integrin $\alpha_L$ I domain polypeptide to thereby isolate immunoglobulin library members that bind to an conformation specific epitope on an integrin $\alpha_L$ I domain polypeptide, e.g., an open conformation. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612).

Additionally, examples of methods and reagents particularly amenable for use in generating and screening antibody display library can be found in, for example, Ladner et al. U.S. Pat. No. 5,223,409; Kang et al. WO 92/18619; Dower et al. WO 91/17271; Winter et al. WO 92/20791; Markland et al. WO 92/15679; Breitling et al. WO 93/01288; McCafferty et al. WO 92/01047; Garrard et al. WO 92/09690; Ladner et al. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) Proc. Natl. Acad Sci. USA 89:3576-3580; Garrad et al. (1991) Bio/Technology 9:1373-1377; Hoogenboom et al. (1991) Nuc. Acid Res. 19:4133-4137; Barbas et al. (1991) Proc. Natl. Acad. Sci. USA 88:7978-7982; and McCafferty et al. Nature (1990) 348:552-554.

Additionally, recombinant anti-integrin $\alpha_L$ I domain polypeptide antibodies, such as chimeric and humanized monoclonal antibodies, comprising both human and non-human portions, which can be made using standard recombinant DNA techniques, can also be used in the methods of the present invention. Such chimeric and humanized monoclonal antibodies can be produced by recombinant DNA techniques known in the art, for example using methods described in Robinson et al. Int'l App. No. PCT/US86/02269; Akira, et al. EP App. 184,187; Taniguchi, M., EP App. 171,496; Morrison et al. EP App. 173,494; Neuberger et al. WO 86/01533; Cabilly et al. U.S. Pat. No. 4,816,567; Cabilly et al. EP App. 125,023; Better et al. (1988) Science 240:1041-1043; Liu et al. (1987) Proc. Natl. Acad Sci. USA 84:3439-3443; Liu et al. (1987) J. Immunol. 139:3521-3526; Sun et al. (1987) Proc. Natl. Acad Sci. USA 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Oi et al. (1986) BioTechniques 4:214; Winter U.S. Pat. No. 5,225,539; Jones et al. (1986) Nature 321:552-525; Verhoeyan et al. (1988) Science 239:15.34; and Beidler et al. (1988) J. Immunol. 141:4053-4060.

In a preferred embodiment, an anti-integrin $\alpha_L$ I domain antibody of the invention binds selectively to an integrin $\alpha_L$ I-domain in the open, high-affinity conformation, e.g., at an epitope that is unique to an activated integrin $\alpha_L$ (also referred to herein as an activation specific epitope). In a preferred embodiment, an anti-integrin $\alpha_L$ I domain antibody of the invention modulates (e.g., inhibits) the binding interaction between an activated integrin $\alpha_L$ I domain and its cognate ligand, e.g. ICAM-1. In another embodiment, an anti-integrin $\alpha_L$ I domain antibody inhibits leukocyte adhesion and/or aggregation. In another embodiment, an anti-integrin $\alpha_L$ I domain antibody of the invention binds selectively to an integrin $\alpha_L$ I-domain in an open conformation, e.g., an LFA-1 I-domain in an open conformation, or a integrin $\alpha_L$ I-domain polypeptide of the present invention.

An anti-integrin $\alpha_L$ I domain antibody (e.g., a monoclonal antibody) can be used in the methods of the invention to modulate the expression and/or activity of an integrin $\alpha_L$ or an integrin $\alpha_L$ I-domain polypeptide. An anti-integrin $\alpha_L$ I domain antibody can also be used to isolate integrin $\alpha_L$ polypeptides, e.g. integrin $\alpha_L$ I-domain polypeptides or fusion proteins, by standard techniques, such as affinity chromatography or immunoprecipitation. In another embodiment, an anti-integrin $\alpha_L$ antibody can be used to remove and/or kill cells expressing activated integrin. Moreover, anti-integrin $\alpha_L$ I domain antibody can be used to detect integrin $\alpha_L$ polypeptides in a particular conformation (e.g., an activated integrin $\alpha_L$), for example, for the localization of stimulated and/or activated leukocytes. Furthermore, an anti-integrin $\alpha_L$ I domain antibody, e.g., an antibody which reacts with or binds an integrin $\alpha_L$ I-domain in an open conformation or a integrin $\alpha_L$ I-domain polypeptide, can be used therapeutically as described herein. Accordingly anti-integrin $\alpha_L$ I domain antibodies can be used diagnostically to monitor protein levels in blood as part of a clinical testing procedure, e.g., to, for example, detect inflammation. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Pharmaceutical Formulations

The invention also provides a composition comprising an integrin $\alpha_L$ I-domain polypeptide or an anti-integrin $\alpha_L$ antibody, e.g., an anti-LFA-1 antibody (or an antigen binding fragment thereof) which selectively binds to an integrin $\alpha_L$ I-domain, e.g., an $\alpha_L$ I-domain in the open conformation, and a pharmaceutically acceptable carrier. The compositions of the invention are used in therapeutic methods of the invention. For example, the invention provides methods for treating or preventing an integrin-mediated disorder (e.g., an inflammatory or autoimmune disorder) in a subject, or for inhibiting the binding of an integrin to a cognate ligand in a subject comprising administering to a therapeutically effective amount of an integrin $\alpha_L$ I-domain polypeptide or anti-integrin $\alpha_L$ antibody (or an antigen binding fragment thereof) which selectively binds to an integrin $\alpha_L$ I-domain. In a preferred embodiment, the integrin $\alpha_L$ I-domain polypeptide binds ligand, e.g. ICAM-1, with high affinity. In another preferred embodiment, the modified integrin $\alpha_L$ I-domain polypeptide for therapeutic use is a soluble polypeptide, e.g., a fusion protein.

It is contemplated that the polypeptide or antibody of the present invention may be used to treat a mammal e.g. a patient suffering from, or predisposed to, a disease or disorder who could benefit from administration of the polypeptide or antibody.

The polypeptide composition or antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the polypeptide or antibody to be administered will be governed by such considerations, and is the minimum amount necessary to prevent, ameliorate, or treat a disease or disorder. The polypeptide or antibody need not be, but is optionally formulated with one or more agents currently used to prevent or treat the disorder in question. The effective amount of such other agents depends on the amount of polypeptide or antibody present in the formulation, the type of disorder or treatment, and other factors discussed above. These are generally used in the same dosages and with administration routes as used hereinbefore or about from 1 to 99% of the heretofore employed dosages.

Therapeutic formulations of the polypeptide or antibody are prepared for storage by mixing the polypeptide or antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

The polypeptide or antibody is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In addition, the polypeptide is suitably administered by pulse infusion, particularly with declining doses of the polypeptide. Preferably the dosing is given by injections, most preferably intravenous or subcutaneous injections, depending in part on whether the administration is brief or chronic.

A pharmaceutical composition is formulated to be compatible with its intended route of administration. Examples of routes of administration include parenteral, intravenous, intradermal, subcutaneous, oral, inhalation, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants, appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Methods for preparation of such formulations will be apparent to those skilled in the art. Suitable examples of sustained-release preparations include semipermeable matrices of solid hydrophobic polymers containing the polypeptide, which matrices are in the form of shaped articles, e.g., films, or microcapsule. Examples of sustained-release matrices include polyesters, hydrogels (for example, poly(2-hydroxyethyl-methacryoate), or poly(vinylalcohol)), polylactides (U.S. Pat. No. 3,773,919), copolymers of L-glutamic acid and γ-ethyl-L-glutamate, non-degradable ethylene-vinyl acetate, biodegradable, biocompatible polymers can be used, such as ethylene vinyl acetate, polyanhydrides, polyglycolic acid, collagen, polyorthoesters, polylactic acid, lactic acid-glycolic acid copolymers such as the LUPRON DEPO™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

For the prevention or treatment of disease, the appropriate dosage of polypeptide will depend on the type of disease to be treated, the severity and course of the disease, whether the polypeptide is administered for preventive or therapeutic purposes, previous therapy, the patient's clinical history and response to the polypeptide, and the discretion of the attending physician. The polypeptide is suitably administered to the patient at one time or over a series of treatments.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Depending on the type and severity of the disease an initial candidate dosage for administration to the patient, whether, for example, by one or more separate administrations, or by continuous infusion, is about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. A typical daily dosage might range from about 1 µg/kg to 100 mg/kg or more. For repeated administrations over several days or longer, depending on the condition, the treatment is sustained until a desired suppression of disease symptoms occurs. However, other dosage regimens may be useful. For example, the protein or polypeptide or antibody can be administered one time per week for between about 1 to 10 weeks, preferably between 2 to 8 weeks, more preferably between about 3 to 7 weeks, and even more preferably for about 4, 5, or 6 weeks.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. The progress of this therapy is easily monitored by conventional techniques and assays.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Method of Treatment

The present invention provides for both prophylactic and therapeutic methods of treating a subject at risk of an integrin $\alpha_L$-mediated ICAM-1 disorder or having an integrin-$\alpha_L$-mediated ICAM-1 disorder such as an inflammatory or immune disorder, and/or a cellular proliferative disorder.

In one aspect, the invention provides a method for preventing in a subject a disease or condition associated with an integrin $\alpha_L$-mediated ICAM-1 disorder by administering to the subject one or more integrin $\alpha_L$ I-domain polypeptides or antibodies of the present invention or modulators thereof. Subjects at risk for an integrin $\alpha_L$-mediated ICAM-1 disorder can be identified by, for example, any or a combination of diagnostic or prognostic assays. Administration of a prophylactic agent can occur prior to the manifestation of symptoms characteristic of the integrin $\alpha_L$-mediated ICAM-1 disorders, such that a disease or disorder is prevented or, alternatively, delayed in its progression. Depending on the type of integrin-mediated disorder, for example, appropriate integrin $\alpha_L$ I-domain polypeptides of the present invention, or modulators or antibodies thereof, can be used for treating the subject. The appropriate agent can be determined based on screening assays described herein.

Another aspect of the invention pertains to methods of treating in a subject a disease or condition associated with integrin $\alpha_L$-mediated ICAM-1 disorder by administering to the subject one or more integrin $\alpha_L$ I-domain polypeptides of the present invention or modulators or antibodies thereof. Depending on the type of integrin-mediated disorder, for example, appropriate integrin $\alpha_L$ I-domain polypeptides of the present invention, or modulators or antibodies thereof, can be used for treating the subject. The appropriate agent can be determined based on screening assays described herein. The present invention provides methods of treating an individual afflicted with a disease or disorder characterized as associated with an integrin $\alpha_L$-mediated ICAM-1 disorder. In one embodiment, the method involves administering an agent (e.g. an integrin $\alpha_L$ I-domain polypeptides of the present invention, an anti-integrin $\alpha_L$ I domain polypeptide antibody), or combination of agents that inhibit native or endogenous integrin $\alpha_L$ from binding to ICAM-1.

This invention is further illustrated by the following examples which should not be construed as limiting. The contents of all references, patents and published patent applications cited throughout this application, as well as the figures and sequence listing are incorporated herein by reference.

EXAMPLES

Example 1

Directed Evolution to Probe Protein Allostery: Integrin I Domains of Unprecedented Affinity Materials and Methods
Yeast Surface Display System The yeast strain used in this study is EBY100[26]. The $\alpha_L$ I domain cDNA coding for residues Asn-129 to Thr-318 was subcloned into the display plasmid pCTCON[31] using NheI and BamHI sites. This results in a fusion protein that contains from N- to C-terminus Aga2, linker, hemagglutinin tag, I domain, and c-myc tag. When expressed, Aga2 is disulfide-bonded to Aga1, which is covalently attached to the cell wall via a phosphatidylinositol glycan tail intermediate[31]. Previously characterized disulfide-bonded, intermediate affinity (IA; L161C/F299C) and high affinity (HA; K287C/K294C) I domain mutants[6] were also cloned into pCTCON. Plasmids were transformed into EBY100 using the EZ-Yeast Transformation Kit (Zymo Research) according to the manufacturer's manual.

Error-Prone and Focused Mutagenesis Libraries

Error-prone libraries were generated by error-prone PCR using a mutagenesis kit (GENEMORPH® II random mutagenesis kit, Strategene) according to the manufacturer's instructions. For the error-prone PCR, oligonucleotide primers 5'CTACGCTCTGCAGGCTAGTG (SEQ. ID. NO. 3) and 5' CATCTACACTGTTGTTATCAGATCTCG (SEQ. ID.

NO.4), annealing ~50 bp upstream and downstream of the I domain cDNA, were used. In focused mutagenesis, to screen for activating mutations at each of the ratchet residues (Leu-289, Phe-292, Leu-295) of the I domain, reverse primers were synthesized (spanning codons for amino acids 278-309 of the I domain) with a codon designation of NNX (N=any of A, T, G, or C; X=wild type nucleotide) for Leu-289, Phe-292, or Leu-295. This allowed substitutions of all 20 amino acids except Asn, Asp, Cys, His, Ile, Phe, and Tyr for Leu-289 and Leu-295, and all except Gln, Glu, Lys, Met, and Trp for Phe-292. The cDNA coding for the I domain was amplified by two-step overlap PCR. First, I domain coding for residues of 129-309 was amplified with a forward primer (annealing to the codons for residues of 129-136) and one of the degenerate reverse primers. In a second step, I domain coding for residues of 129-318 was amplified with a forward and a reverse primer (annealing to the codons for residues 300-318) using the product from the first step as a template.

Amplified I domain cDNA was concentrated to 1-2 μg/μl in water and pCTCON was linearized by digestion with NheI and BamH1, and concentrated to 0.5 μg/μl in water. Mixtures of 1 μg of the cDNA (~3×10$^{12}$ copies) and 0.5 μg of the linearized vector (~10$^{11}$ copies) in 5 μl water were transferred to a cuvette containing ~10$^8$ yeast cells in 50 μl of 10 mM Tris, pH 7.5, 270 mM sucrose, 1 mM MgCl$_2$. Electroporation was performed according to the published protocols[31]. Transformation efficiency was 2% estimated by the number of colonies on SD-CAA plate (2% w/v agar plate containing SD-CAA: 2% w/v dextrose, 0.67% w/v yeast nitrogen base, sodium phosphate buffer, pH 6.6, casamino acids without ADE, URA, TRP). Based on the assumption that the majority of the mutagenized I domain cDNAs transformed into cells are unique because of the much larger number of copies of DNA than of transformed cells, the library size was estimated from the transformation efficiency to be 2% of 10$^8$ cells or 2×10$^6$.

After transformation, cells were grown in 5 ml of SD-CAA media at 30° C. with shaking for 24 h. In order to induce protein expression, cells in 1 ml of SD-CAA were spun down, and transferred to 1 ml of SG-CAA media (2% w/v galactose, 0.67% w/v yeast nitrogen base, sodium phosphate buffer, pH 6.6, casamino acids without ADE, URA, TRP), and cultured for 24 h at room temperature with shaking. To estimate a mutation rate in the error-prone I domain library, five colonies from the SD-CAA plate each were transferred to 1 ml of SD-CAA, cultured for 24 h at 30° C. with shaking, and the plasmids were purified using a Zymoprep kit (Zymo Research) for sequencing. The mutation rate was ~3 mutations per 1,000 nucleotides, which upon translation corresponded to ~7 mutations per 1000 amino acids.

Immunofluorescence Flow Cytometry

Cells that were cultured only in SD-CAA or further induced in SG-CAA were harvested, washed with 100 μl of labeling buffer (PBS, 0.5% BSA, 10 mM MgCl$_2$), and then incubated with ligands at 10 μg/ml in 50 μl of the labeling buffer for 20 min with shaking at 30° C. in a 96-well V-bottom plate. Ligands used in this study were anti-c-myc antibody 9E10 (Santa Cruz Biotechnology, CA) and anti-hemagglutinin antibody 12CA5 (Roche Applied Science), $\alpha_L$ I domain-specific antibodies TS1/22 and MEM83[32], and ICAM-1-Fcγ (ICAM-1 residues of 1-480 fused to the Fc of human IgG, R&D Systems). After incubation with the primary ligands, cells were washed once in 100 μl of the labeling buffer and incubated with the fluorescence-conjugated secondary antibodies at 5 μg/ml in 50 μl of the labeling buffer for 20 min at 4° C. Finally, cells were washed once in 100 μl and suspended in 100 μl of the labeling buffer for flow cytometry (FACScan, BD Biosciences).

To calculate specific fluorescence intensity (SFI), the mean fluorescence intensity (MFI) of uninduced clones was subtracted from the MFI of induced clones. Since the SFI of ICAM-1 is affected both by the affinity to the I domains and the difference in the level of I domain expression, the SFI of ICAM-1 was corrected by dividing it by the SFI of 9E10 mAb to c-myc tag, and these values were defined as adjusted SFI (ASFI). For example, the ASFI of ICAM-1 is computed as:

[MFI (ICAM-1) of induced−MFI (ICAM-1) of uninduced]/[MFI (9E10) of induced−MFI (9E 10) of uninduced]

Then the ASFI of ICAM-1 of clones were compared to that of the clone expressing the high affinity I domain mutant (HA), e.g., the % HA-ASFI of clone m1=100×ASFI (clone m1)/I ASFI (HA).

Magnetic Cell Sorting

Sorting of the I domain library was performed with a magnetic cell sorter (MACS LS Column, Miltenyi Biotec). The I domain library (~10$^8$ cells) induced in 1 ml of SG-CAA was spun down, washed with 1 ml of the labeling buffer (PBS, 0.5% BSA, 10 mM MgCl$_2$), and incubated with 5 μg/ml of ICAM-1-Fcγ in 200 μl of the labeling buffer for 20 min with shaking at 30° C. in a 14 ml polypropylene tube. After incubation with primary ligands, cells were washed once with 1 ml of the labeling buffer, and incubated in 80 μl of the labeling buffer and 20 μl of mouse anti-human IgG microbeads (Miltenyi Biotec) for 20 min at 4° C. Cells were washed with 1 ml of the labeling buffer, resuspended in 1 ml, and were sorted according to the manufacturer's manual. Enriched cells were expanded for 24-36 h in 1 ml of SD-CAA at 30° C. with shaking, and ~10$^8$ cells were induced in 1 ml of SG-CAA for 24 h at room temperature with shaking for flow cytometry and, if necessary, for the next round of sorting.

Expression of Soluble I Domains and Surface Plasmon Resonance Measurements

Mutant I domains (F265S, F292A, F292G, F265S/F292G, and HA) with residues of Asn-129 to Tyr-307 were expressed in *Escherichia coli* BL21 (DE3) (Novagen), refolded, and purified as described previously[6]. ICAM-1-Fcγ-coupled or mock-coupled CM5 sensor chip as control was prepared using the amine coupling kit (BIAcore, Piscataway, N.J.), as described previously[33]. Surface plasmon resonance was measured using Biacore 3000. I domains were injected over the chip in 20 mM Tris HCl, pH 8.0, 150 mM NaCl, 10 mM MgCl$_2$, at a flow rate of 10 μl/min at room temperature.

Calculation of the Percent Solvent Exposure of the Residues in I Domain

Solvent accessible surface area of each residue in the closed and open structure of the I domain was calculated using the program, areaimol within the CCP4 suite[34] with default parameters. Percent solvent exposure of residues was calculated by dividing the solvent accessible surface area within the I domain by the residue-specific maximum solvent accessible surface area[35]. Because the closed $\alpha_L$ I domain crystal structures differ from one another in the α7-helix due to unusual crystal packing interactions, the closed $\alpha_L$ I domain structure was modeled based on the crystal structure of 1LFA and 1ZON, as was described previously[8]. The structure of the α7-helix of the open $\alpha_L$ I domain (1 MQ9) was similarly modeled[8].

Cell Adhesion Assays

The effect of the soluble I domain mutants on blocking the adhesion of human T lymphocytes to ICAM-1-Fcγ coated surfaces was quantified by the V-bottom adhesion assay[36, 37]. V-bottom 96-well plates (Corning) were coated with ICAM-1-Fcγ (10 µg/ml in PBS, pH 7.4) or with 2% BSA as a control at 4° C. overnight, and then blocked with 2% BSA for 1 h at 37° C. After the incubation, plates were washed once with PBS, and the wild-type, disulfide-bonded HA, and F265S/F292G were added to ICAM-1-Fcγ coated wells at 0.01-10 µM concentration in 50 µl of L15 medium, 2.5% FBS. Lymphocytes were isolated and cultured in RPMI supplemented with 10% FBS and PHA (1 µg/ml) for 3 days, followed by culture in IL-2 (20 ng/ml) for 3-6 days as described[38]. Right before the assay, cells were washed once with L15, 2.5% FBS and resuspended at $10^6$ cells/ml. Then phorbol ester 12-tetradecanoylphorbol-13 acetate (PMA) at 100 ng/ml and 2',7'-bis-(2-carboxyethyl)-5-(and-6)-carboxyfluorescein acetoxymethyl ester (BCECF-AM) at 2 µg/ml were added to the cell suspension for activation and labeling, respectively. After incubation at 37° C. for 30 min, cells were washed twice in L15, 2.5% FBS, and allowed to recover for 5 min at 37° C., and in 50 µl of L15, 2.5% FBS were added to the wells. The plates were immediately centrifuged at 200 g for 15 min at room temperature. Nonadherent cells that accumulated at the center of the V-bottom due to centrifugation were quantified by a fluorescence plate reader (Spectra MAX Gemini XS, Molecular Devices) with the excitation at 485 nm and the emission at 538 nm. The percent inhibition of cell adhesion to ICAM-1 by I domains was calculated from the fluorescence intensity of experimental measurements (F), the positive control coated with ICAM-1-Fcγ without added I domains ($F_{ICAM-1}$), and the negative control coated with BSA alone ($F_{BSA}$): $100\times(F-F_{ICAM-1})/(F_{BSA}-F_{ICAM-1})$.

Homotypic Aggregation

The effect of the soluble I domains on blocking homotypic aggregation of JY EBV-transformed B lymphoblastoid cells was evaluated by a qualitative aggregation assay (score 0 to 5) essentially as previously described[39], except I domains were used as inhibitors instead of mAb. Aggregation scoring was evaluated at 1 h after incubation of cells with PMA and I domains.

Transmigration Assay

The effect of the soluble I domains on trans-endothelial migration (TEM) was determined essentially as previously described[38]. Endothelial monolayers were prepared by plating 50,000 primary human dermal microvascular endothelial cells (HDMVECs; Cambrex) per well in 24-well culture plates containing fibronectin (10 µg/ml)-coated glass coverslips followed by culturing for 48-72 h in EBV-2 complete media (Cambrex). Prior to each experiment, HDMVECs were activated for 12 h with TNF-α (100 ng/ml). HDMVECs were then washed three times in Buffer-A (Hank's balanced salt solution supplemented with 20 mM Hepes, pH 7.2 and 1% human serum albumin) and then pre-incubated for 5 min at 37° C. in Buffer-A alone (control) or Buffer-A containing the wild-type, HA, and F265S/F292 I domains (1 µM) or RR1/1[40] or MHM24[41] mAbs (0.33 µM). IL-2-cultured primary human lymphocytes were pelleted, resuspended at 100,000 cells/ml in 500 µl Buffer A containing I domains or mAbs as stated above and then added to HDMVECs and incubated at 37° C. for 10 min. Samples were fixed in 3.7% formaldehyde in PBS for 5 minutes and stained with Cy3-conjugated mAb TS2/4 for leukocyte $\alpha_L\beta_2$ and with Alexa488-conjugated mAb IC1/11 for endothelial cell ICAM-1, as well as for F-actin (phalliodin-Alexa647; Molecular Probes), as described[38]. Imaging was then conducted using Biorad Radiance 2000 Laser-scanning confocal microscope system (Hercules, Calif.). For each condition complete Z-stacks (0.5 µm thickness) were obtained in each of ten randomly selected fields. Using LaserSharp 2000 software (Biorad) Z-stacks were analyzed (based on previously described criteria[38]) to determine the number of cells in the process of, or having completed, diapedesis. Percent inhibition of transmigration was calculated as: 100×(1−fraction of TEM in the presence of I domains or mAbs/fraction of TEM in control).

Introduction

Here we have asked whether directed evolution, an approach based on random mutagenesis coupled with functional screening, and requiring no a priori knowledge of protein structure, could be used to identify key residues in the transmission of allostery within the I domain. Several systems such as mRNA and ribosome display[20, 21], phage display[22], and cell-surface display[23-25] have been used for engineering high affinity peptides and proteins. Yeast surface display offers the advantage of eukaryotic biosynthetic and secretory machinery and has been used successfully to express many mammalian proteins[24, 26-30]. To date, yeast surface display has been applied primarily to enhance protein expression and stability, and to engineer antibodies with improved affinity. Thus far, none of the directed evolution systems have been used to study protein allostery. In this study, we have chosen the $\alpha_L$ I domain as a model system, and demonstrate that directed evolution using a yeast display system can be used to probe protein allostery with great efficiency. Furthermore, we have constructed an allosteric mutant with an unprecedented 200,000-fold increase in affinity.

Results

Expression and Affinity Selection of I Domain Libraries

As positive controls, wild-type I domain, and disulfide-bonded, intermediate affinity (IA) and high affinity (HA) mutant I domains were displayed on yeast. Good display on the yeast cell wall was shown by the binding of the anti-hemagglutinin (12CA5) and anti-c-myc (9E10) antibodies and I domain-specific antibodies TS1/22 and MEM83 (FIG. 1 and not shown). Binding was also measured of ICAM-1-Fcγ chimera (FIG. 1). Binding was undetectable to the wild-type I domain, and ICAM-1 bound 56±19% as well to the IA as to the HA I domain as measured by adjusted specific fluorescence intensity (ASFI).

Next, the yeast display library was tested for the binding of antibodies and ICAM-1. Binding of 12CA5, 9E10, TS1/22, and MEM83 mAbs was reduced significantly after error-prone mutagenesis (FIG. 1 and not shown). Only 30% of cells in the mutant library bound to the 9E10 mAb, compared to 80% for the wild-type I domain prior to mutagenesis. Binding of the I domain-specific mAb MEM83 was reduced much more; this is as expected from the experimentally determined mutation rate of 7 per 1,000 amino acids, because a fraction of the mutations will affect proper folding of I domain. The I domain mutant library was then selected by magnetic cell sorting (MACS) for binding to ICAM-1. The majority of the cells in the enriched library bound to 9E10 and MEM83 mAbs and to ICAM-1 (FIG. 1), suggesting that the vast majority of selected clones contained mutations that stabilized the high-affinity, open conformation of the $\alpha_L$ I domain. When the same mutant library was selected with ICAM-1-Fcγ, multiple cycles were needed to enrich for positive cells. After three cycles, the percentage of cells that bound to 9E10 and MEM83 mAbs, and to ICAM-1 was comparable (FIG. 1).

Activating Mutations in the Error-Prone PCR Library

A total of twenty-five yeast colonies were picked from SD-CAA plates from the libraries selected with ICAM-1-Fcγ. These clones were tested for binding of ICAM-1-Fcγ, and sequenced (Table 1). Of these, 15 had unique sequences and were designated as m1 to m15, and all bound ICAM-1 better than wild-type (Table 1). Five clones contained single mutations, and the remainder contained 2-5 mutations each (Table 1). From the clones containing multiple mutations, one to three residues were selected and independently tested as a single substitution (designated with a, b, or c suffix) or independently isolated from the ratchet residue library (see below).

Some clones containing single mutations (F265S, L274I, and F277L) showed higher binding of ICAM-1 than clones containing these and additional mutations. In contrast some single mutants that were made showed lower binding to ICAM-1 than their parental multiply mutant clones, suggesting either that the wrong residues were selected for single substitutions, or that the activating effect of the mutations were inter-dependent (e.g., L295P and Q303R in m11). The significance of the location of these mutations for understanding I domain allostery is highlighted in the Discussion.

Activating Mutations in the Ratchet Residue Library

Three residues in the β6-α7 loop of the I domain alternatively occupy the same hydrophobic pocket in the closed, intermediate, and open conformation[6], and are termed "ratchet" residues: Leu-289, Phe-292, and Leu-295 (Jin et. al. 2006 PNAS 103: 5758-63). Mutations in each of these ratchet residues were selected from the error-prone PCR library that increased affinity for ICAM-1 (m6, m7, m8, m9, and m11 in Table 1). To obtain higher saturation of mutagenesis of ratchet residues, oligonucleotides randomized in the first two bases of each ratchet residue were used to construct a focused library, and eleven unique clones designated as f1 to f11 were selected (Table 1). From three to four substitutions that activated binding to ICAM-1 were isolated at each ratchet position. The particular residues that were selected suggest that the small amino acids Gly and Ala, Pro, and the large amino acid Trp are particularly activating at the ratchet positions (Table 1).

Kinetics of Binding of Soluble I Domains to ICAM-1

Figure 2:
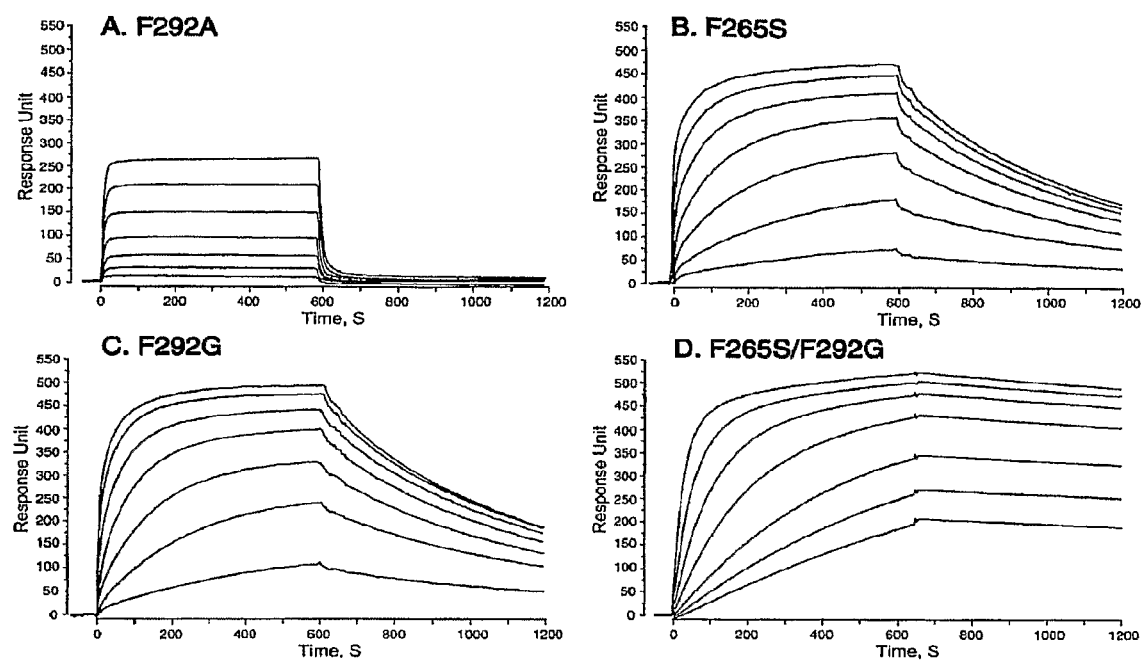
FIG. 2 shows binding of $\alpha_L$ I domains to ICAM-1 measured with surface plasmon resonance (Biacore). Sensograms show the binding of the I domain mutants (F292A, F265S, F292G, and F265S/F292G) to ICAM-1-Fcγ-coated sensor chip. In all sensograms, the signals from the control surface, as described in Materials and Methods, were subtracted. I domain mutants were injected in a series of concentrations starting from 100 µM for F292A and 1 µM for F292G, F265S, and F265S/F292G, and the subsequent concentrations were by two-fold serial dilutions.

Several of the most activating mutants were expressed in *Escherichia coli* and refolded in order to measure the kinetics of binding to ICAM-1 by surface plasmon resonance (FIG. 2). Data are shown in Table 2, and for comparison are shown kinetics measured for the wild-type and disulfide-bonded IA and HA mutants in a previous study[6], and for the same disulfide-bonded HA mutant in the current study. The $K_d$ of the HA mutant in the current study (105±50 nM) is within experimental error of that measured previously (150±16 nM), although we would expect to obtain a slightly higher affinity, as observed, because we use 10 mM $Mg^{2+}$ instead of 1 mM $Mg^{2+}$, and $Mg^{2+}$ is one of the three components in the I domain:$Mg^{2+}$:ICAM-1 complex.

All the single mutants, F265S, F292A, and F292G, exhibited an association rate to ICAM-1 in a similar range of 9,500-16,000 $M^{-1}s^{-1}$. The double mutant, F265S/F292G showed a 2-fold higher $k_{on}$ of 25,000 $M^{-1}s^{-1}$. These association rates are lower than observed for the IA and HA mutants of 105,000-133,000 $M^{-1}s^{-1}$. In contrast to the association rates, the mutants isolated in this study differ very markedly one from another in their dissociation rates. The F265S and F292G mutants showed a 100-fold slower dissociation rate than the F292A mutant. The double mutant, F265S/F292G exhibited a further 10-fold decrease in dissociation rate compared to the F265S and F292G single mutants. The dissociation rate for the double mutant was slower than the HA I domain by close to 100-fold.

The $K_d$ of the single F265S and F292G mutants of about 100 nM is similar to that of the HA I domain. Remarkably, the $K_d$ of the double F265S/F292G mutant is 6 nM, which corresponds to an increase of 200,000-fold in affinity compared to the wild-type I domain. All of the I domain mutants were monomeric in solution as assessed by size-exclusion chromatography, and therefore the slower dissociation-rate was not affected by avidity modulation.

Figure 3:
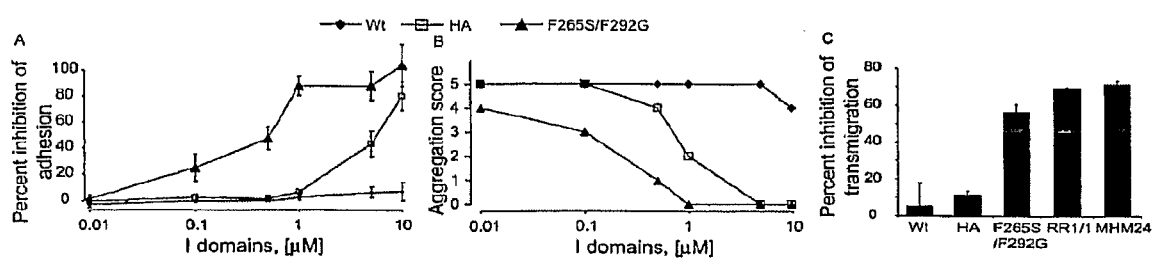
FIGS. 3A-3C show soluble I domains as inhibitors for LFA-1-ICAM-1 interaction.

Soluble I Domains as Inhibitors of Adhesion, Homotypic Aggregation, and Transmigration The potential to antagonize lymphocyte function-associated antigen 1 (LFA-1)-dependent lymphocyte adhesion to ICAM-1 with soluble I domains was examined in vitro. Consistent with the differences in affinity measured by surface plasmon resonance, the F265S/F292G mutant ($IC_{50}$=0.35 μM) was much more potent than the disulfide-bonded HA mutant ($IC_{50}$=5.3 μM) in blocking the adhesion of PMA activated lymphocytes to ICAM-1 coated surfaces (FIG. 3A). The wild-type I domain gave no inhibition in the same assay.

Homotypic aggregation of lymphocytes stimulated by PMA occurs through the interaction between LFA-1 and ICAMs[39]. When the soluble I domains were tested as inhibitors for blocking the aggregation of JY lymphoblastoid cells, the wild-type I domain was slightly effective only at the highest concentration (FIG. 3B). The HA I domain mutant at as low as 5 μM completely inhibited the aggregation. In contrast, the F265S/F292G mutant at 1 μM completely blocked aggregation, and at 0.5 μM less than 10% of cells were in aggregates. Even at 0.01 μM, the F265S/F292G was effective in inhibiting the formation of large and compact clusters, which were already observed at 0.1 μM of the HA I domain.

Adhesion and subsequent migration of leukocyte across vascular endothelium, a process referred to as transendothelial migration, is required for emigration from the bloodstream. The interaction between LFA-1 on leukocytes and ICAM-1 and ICAM-2 on endothelium has been identified as important for this process[38]. When the I domains were tested at 1 μM, the F265S/F292G mutant was found to be much more efficient than the HA mutant I domain at blocking transmigration (FIG. 3C). The amount of inhibition by the F265S/F292G mutant at 1 μM was comparable to that of the anti-ICAM-1 antibody RR1/1 and the anti-LFA-1 I domain antibody MHM24, which were used at 0.33 μM and are bivalent.

Discussion

Expert design and computational algorithms have previously been used to identify residues that when mutated could alter the conformational equilibrium of proteins under allosteric control. However, neither method has been used systematically to examine allostery. For example, our previous computational study of I domains aimed only to repack the hydrophobic core of the open conformation, not to identify residues important in allostery, and involved simultaneous mutation of 8 to 13 residues[19]. In this study, we tested whether directed evolution could be used 1) to engineer high affinity in a protein in which affinity is allosterically regulated and 2) to structurally probe allosteric pathways within a protein.

Our results show that directed evolution using a yeast surface display system optimized for large-scale mutagenesis and high throughput screening is an efficient method to identify key residues in the transmission of allostery within the I domain. From 25 clones that were isolated with ICAM-1, all previously speculated or tested hot spots based on expert inspection were found (Phe-265[2], Leu-289[5], Phe-292[2,5], and Leu-295[5]), together with many new positions (Ile-258, Gly-262, Leu-274, Phe-277, Ile-288, Glu-293, and Ile-309). Furthermore, using focused mutagenesis of the ratchet positions, we found that the identity of the substituting amino acid was markedly more important than previously suspected. None of the activating mutations were found in the ICAM-1-binding interface, supporting our hypothesis that they are allosteric mutations that shift the conformational equilibrium toward the open, high affinity conformation.

The mutations found here identify residues that are key in the shape-shifting pathway that connects the ligand binding site, composed of the MIDAS loops, to the α7-helix which communicates allostery to neighboring domains in intact integrins. In the transition of the MIDAS from closed to open conformation, the MIDAS metal moves ~2 Å toward Thr-206 on the α3-α4 loop and away from Asp-239 in the β4-α5 loop (Jin et. al. 2006 PNAS 103: 5758-63). This movement results in shifts of Thr-206 to the primary coordination sphere and Asp-239 to the secondary coordination sphere of the $Mg^{2+}$ ion, which therefore increases its electrophilicity for ligand. The MIDAS loops undergo closely linked changes; these form coordinations to the $Mg^{2+}$ ion and also form the ligand-binding pocket, which is thus restructured. The α1-helix, particularly near its N-terminal or "top" end, and the β1-α1 loop bearing the metal-coordinating residues Ser-139 and Ser-141, move inward along with the $Mg^{2+}$ ion. Furthermore, there is a backbone flip at Gly-240 of the β4-α5 loop, enabling its Asp-239 side chain to alter metal ion coordination and its Glu-241 side chain to form a crucial salt-bridge to ICAM-1 (Jin et. al. 2006 PNAS 103: 5758-63). These changes all involve MIDAS loops and are directly involved in ligand binding; we will refer to the region containing them as the region of "binding allostery" (FIG. 4). Remarkably, none of the allosteric activating mutations we have selected map to the region of binding allostery; instead they define another region that we term the region of "switch allostery". The switch allostery region corresponds to a single segment of primary structure containing secondary structure elements β5, α6, β6, and α7 (FIG. 4).

Our findings provide insights into how the switch and binding allostery regions are coupled. The switch allostery region undergoes a shearing motion with respect to the remainder of the I domain, including the binding allostery region (Jin et. al. 2006 PNAS 103: 5758-63). Previously, the importance of movements of key residues and isolated segments of the switch allostery regions have been discussed[10, 42], but not its shearing motion as a whole. For example, the closed and open conformations have been compared using superposition of β-strands 1-5; however, β-strand 5 belongs to the switch allostery region. In allostery, the twist of the central β-sheet increases, with a significant increase in twist between β-strands 4 and 5, and a marked increase between β-strands 5 and 6 (Jin et. al. 2006 PNAS 103: 5758-63). This twisting/shearing motion normal to the plane of the central β-sheets is accompanied by movements across the entire interface, as shown in the en-face view in Jin et. al. 2006 PNAS 103: 5758-63. Indeed, the allosteric mutations we have identified are distributed from one side of this interface to the other, demonstrating that residues throughout this extensive interface participate in balancing the energy between the open and closed conformational states.

In the closed conformation, the residues identified by mutation form a continuous chain of contacts around one rim of the interface (Jin et. al. 2006 PNAS 103: 5758-63). The hydrophobic side chains of Phe-277 and Leu-274 in the α6-helix and Ile-258 in the β5-strand pack against one another on one side of the switch allostery-binding allostery interface. This hydrophobic interface extends by contacts with Leu-274 to the side chains of Phe-265 in the β5-α6 loop and Ile-288 in the β6-strand. Furthermore, backbone hydrogen bonds connect Phe-265 to Gly-262, and in turn Gly-262 to Leu-289. Leu-289 is also covalently linked to Ile-288 in the above hydrophobic cluster. Leu-289 is one of the β6-α7 loop ratchet residues. In the closed conformation, Leu-289 packs closely with ratchet residues Phe-292 and Leu-295, and Leu-295 is in the hydrophobic ratchet pocket which is formed in part by Phe-292 and Leu-289. The residues identified by allosteric mutations thus are all structurally contiguous, and are linked by hydrophobic packing, backbone hydrogen bonds, and peptide bonds. These residues outline one rim of the interface between the regions of switch and binding allostery. Notably, the shearing motions between these regions are large along this rim, and markedly lesser at the opposite side of the interface where the switch allostery region connects to the remainder of the I domain at the α5-β5 loop.

During shearing of the switch allostery region to the open conformation, interaction between the hydrophobic residues Phe-277, Leu-274, Ile-258, Phe-265, and Ile-288 is maintained, although swinging away of the Ile-288 side chain lessens its contacts. Furthermore, a change in backbone orientations at Gly-262 severs its hydrogen bonds to Phe-265 and Leu-289, as Leu-289 moves into the ratchet pocket (Jin et. al. 2006 PNAS 103: 5758-63).

Our mutational findings demonstrate that the region that regulates allostery is larger than previously suspected, and extends all the way to Phe-277 at one end of the rim. Notably, the F277L and L274I mutations, although conservative in nature and far from the ratchet pocket, increased binding of ICAM-1 as much as the F265S and F292G mutations (Table 1). The importance of hydrophobic packing at Phe-277 and Leu-274 had not previously been noted in discussion of I domain allostery. A role for Gly-262 in $α_L$ or the equivalent Gly-272 in $α_M$ or Leu-283 in $α_2$ had also not been previously noted. The two major clusters of hydrophobic residues in the switch allostery region are kept in a fixed position relative to one another in the closed conformation by backbone hydrogen bonds that link Leu-289, Gly-262, and Phe-265. Breakage of these backbone hydrogen bonds in the open conformation is required in the rearrangements at Leu-289 and Phe-265 and their hydrophobic clusters. Equivalent backbone hydrogen bonds are present and broken in the closed and open conformations, respectively, of the $α_M$ and $α_2$ I domains. These findings emphasize the ability of directed evolution to shed light on protein allostery.

The directed evolution approach allowed us to make the unexpected observation that Gly and Ala substitutions for the ratchet residues Leu-289 and Phe-292 differ markedly in affinity enhancement (Table 1). Phe-292 in the closed position of the α7-helix is buried in a hydrophobic pocket and becomes exposed to solvent as the α7-helix moves downward to the open position (Jin et. al. 2006 PNAS 103: 5758-63). The lower energetic penalty for exposure of Ala compared to Phe, estimated from partition data for benzene, is 2.9 kcal/mol[43], corresponding to a 135-fold stabilization of the open conformation. This is in close agreement with the observed increase in affinity of 75-fold of the F292A mutant (Table 2). By contrast, the 170-fold higher affinity of the F292G mutant compared to the F292A mutant (Table 2) cannot be explained by exposure of the extra methylene group present in Ala compared to Gly[43], which is only predicted to cause a 3-fold higher affinity. The substantially larger observed increase in affinity for F292G compared to F292A may therefore be derived from the ability of Gly to assume a wider range of phi/psi backbone angles[44], and backbone change at residue 292. A change in backbone at residue 289 may also explain the substantially higher affinity for ICAM-1 of L289G than L289A as observed by flow cytometry. The effect of Gly substitution accompanied by backbone change is computationally very challenging to predict, since current algorithms do not consider backbones that have not been previously seen experimentally. We also found that Pro substitutions at all three ratchet residues were activating, with the largest enhancement at Leu-289. Activation by proline substitution at residue 289 can be explained by the preference for the backbone angles adopted by proline. The phi angle for proline is constrained at −63±15° by the covalent bond to its backbone nitrogen[45]; this is compatible with the phi angle at residue 289 of −58° in the open conformation, but not with the phi angle of −116° in the closed conformation.

The increases in affinity we have achieved are unprecedented in protein engineering. Previously, substantial improvement in ligand-binding affinity (~100-fold) has been demonstrated by point mutations in a maltose binding protein[46], that stabilize the ligand-bound conformation. In our previous studies with the $\alpha_L$ I domain, an increase of 10,000-fold in affinity to ICAM-1 was achieved by introducing a pair of cysteines to form a disulfide-bond that stabilizes the open conformation[5]. However in protein-protein interactions lacking allosteric activation, mutations in the binding interface typically increase affinity by less than 100-fold[47, 48]. By combining point mutations of F265S and F292G, each of which led to a 1,000-fold decrease in dissociation-rate and to a 10,000-fold increase in affinity, we engineered the double mutant F265S/F292G, with an unprecedented 200,000-fold increase in affinity to ICAM-1. Compared to the disulfide-bonded HA I domain mutants, the kinetics of the mutants isolated in this study (F265S, F292G, and F265S/F292G) were markedly different. The slower association rate of these mutants may indicate that they are less efficient than the HA mutant in adopting the ligand competent conformation prior to ICAM-1 binding. The significantly slower dissociation rate of the mutants described here may indicate some subtle improvements in the ligand-bound structures, and as a consequence, a lower free energy of the complex.

The remarkable enhancements achieved here by directed evolution bring the affinity of I domains into the range required for effective biotherapeutics. Integrins that contain I domains are important therapeutic targets in inflammation, autoimmunity, and transplantation[49]. We found that in assays of lymphocyte adhesion to ICAM-1, transmigration through endothelium, and homotypic aggregation, the F265S/F292G mutant was 10-fold or more effective than the HA I domain, which has previously been demonstrated to be potent in antagonizing lymphocyte adhesion and homing to peripheral lymph nodes in vivo[5]. The higher potency of the F265S/F292G mutant can be attributed to its 20-fold higher binding affinity than the HA mutant.

We have demonstrated that the identification of mutational hot spots provides important information on the interfaces in proteins that transmit allostery and regulate the difference in free energy between conformational states. The method described here can be readily extended to the study of allostery in other proteins, and will be particularly useful in studying proteins where no structural information is available, or where the structure of only one conformer is known. The I domains optimized for the binding to target ligands can facilitate structural studies including NMR and X-ray crystallography studies of I domains complexed with ligands. Furthermore, high-affinity allosteric mutants can be used directly as biotherapeutics or to isolate therapeutic antibodies specific for a particular conformational state.

TABLE 1

ICAM-1 binding to I domains

| Clones[a] | Mutations[b] | ICAM-1 (% ASFI of HA) |
|---|---|---|
| Wild-type | | 0 |
| m1 | I258T (1; 0) | 10 |
| m2 | I258T, T267A, F277A | 10 |
| m3 | G262E (10; 8) | 4 |
| m4 | F134L, K252E, F265S | 31 |
| m5 | L274I, S279T | 51 |
| m5a | L274I (1; 0) | 91 |
| m6 | F209Y, L289P (7; 7) | 33 |
| m7 | F292S (7; 78) | 47 |
| m8 | F292S, P281E | 54 |
| m9 | F292S, Y177R, L204Q | 28 |
| m10 | F265L, E293G, K294E, K296E, V308I | 16 |
| m10a | F265L (4; 11) | 0 |
| m10b | E293G (52; 68) | 4 |
| m11 | L295P (0; 8), Q303R | 107 |
| m11a | Q303R (31; 33) | 0 |
| m12 | I150T, G246V, F299L, I309T | 27 |
| m12a | I150T (0; 0) | 0 |
| m12b | F299L (17; 32) | 0 |
| m12c | I309T | 17 |
| m13 | F265S | 123 |
| m14 | I288N (56; 3) | 14 |
| m15 | F277L, I288T | 30 |
| m15a | F277L (1; 0) | 110 |
| f1 | L289A | 1 |
| f2 | L289G | 74 |
| f3 | L289P | 24 |
| f4 | L289W | 51 |
| f5 | F292A | 29 |
| f6 | F292G | 91 |
| f7 | F292P | 5 |
| f8 | L295A | 25 |
| f9 | L295P | 5 |
| f10 | L295Q | 4 |
| f11 | L295W | 81 |

Clones isolated from the error-prone PCR library are designated as m1 to m15. Clones identified by focused mutagenesis are designated as f1 to f11. Clones tested as single substitutions are designated by suffix a, b, and c after the names of the parental clones.
The numbers in the parentheses, separated by a semi-colon, are the percent solvent exposure of wild type residues in the closed and open I domain structure.

TABLE 2

Kinetics of the binding of the soluble I domains to ICAM-1 measured by Biacore[a]

| I domain | $k_{on}$ ($M^{-1}s^{-1}$ × $10^{-3}$) | $k_{off}$ ($s^{-1}$) | $K_D$ (μM) |
|---|---|---|---|
| Wild-type[b] | 3.1 ± 0.1 | 4.6 ± 0.36 | 1500 ± 200 |
| IA[b] | 133 ± 10 | 0.43 ± 0.07 | 3 ± 0.44 |
| HA[b] | 115 ± 7 | 0.014 ± 0.001 | 0.15 ± 0.016 |
| HA | 105 ± 49 | 0.011 ± 0.0003 | 0.105 ± 0.05 |
| F265S | 11.8 ± 0.9 | 0.0017 ± 0.0003 | 0.145 ± 0.031 |
| F292A | 9.5 ± 1.2 | 0.19 ± 0.005 | 20.0 ± 0.8 |
| F292G | 16.0 ± 0.8 | 0.0019 ± 0.0004 | 0.119 ± 0.017 |
| F265S/F292G | 25.0 ± 0.76 | 0.00015 ± 0.000003 | 0.006 ± 0.0002 |

The values shown in the table are mean ± SD from three independent measurements. The parameters of $k_{on}$, $k_{off}$, and $K_d$ were calculated by fitting the 1:1 Langmuir binding model to the Biacore sensogram.
The values were from the previous studies [6].

The references cited below and throughout the specification are incorporated herein in their entirety.

REFERENCES

1. Volkman, B. F., Lipson, D., Wemmer, D. E. & Kern, D. Two-state allosteric behavior in a single-domain signaling protein. Science 291, 2429-2433. (2001).
2. Li, R., Rieu, P., Griffith, D. L., Scott, D. & Arnaout, M. A. Two functional states of the CD11b A-domain: Correlations with key features of two Mn2+-complexed crystal structures. J. Cell Biol. 143, 1523-1534 (1998).
3. Huth, J. R. et al. NMR and mutagenesis evidence for an I domain allosteric site that regulates lymphocyte function-associated antigen 1 ligand binding. Proc. Natl. Acad. Sci. U.S.A. 97, 5231-5236 (2000).
4. Aquilina, A. et al. A novel gain-of-function mutation of the integrin alpha2 VWFA domain. Eur J Biochem 269, 1136-1144 (2002).
5. Shimaoka, M. et al. Reversibly locking a protein fold in an active conformation with a disulfide bond: integrin aL I domains with high affinity and antagonist activity in vivo. Proc. Natl. Acad. Sci. U.S.A. 98, 6009-6014 (2001).
6. Shimaoka, M. et al. Structures of the aL I domain and its complex with ICAM-1 reveal a shape-shifting pathway for integrin regulation. Cell 112, 99-111 (2003).
7. McCleverty, C. J. & Liddington, R. C. Engineered allosteric mutants of the integrin aMb2 I domain: structural and functional studies. Biochem. J. 372, 121-127 (2003).
8. Jin, M., Andricioaei, I. & Springer, T. A. Conversion between three conformational states of integrin I domains with a C-terminal pull spring studied with molecular dynamics. Structure 12, 2137-2147 (2004).
9. Lee, J.-O., Rieu, P., Arnaout, M. A. & Liddington, R. Crystal structure of the A domain from the a subunit of integrin CR3 (CD11b/CD18). Cell 80, 631-638 (1995).
10. Lee, J.-O., Bankston, L. A., Arnaout, M. A. & Liddington, R. C. Two conformations of the integrin A-domain (I-domain): a pathway for activation? Structure 3, 1333-1340 (1995).
11. Qu, A. & Leahy, D. J. Crystal structure of the I-domain from the CD11a/CD18 (LFA-1, aLb2) integrin. Proc. Natl. Acad. Sci. U.S.A. 92, 10277-10281 (1995).
12. Qu, A. & Leahy, D. J. The role of the divalent cation in the structure of the I domain from the CD11a/CD18 integrin. Structure 4, 931-942 (1996).
13. Kallen, J. et al. Structural basis for LFA-1 inhibition upon lovastatin binding to the CD11a I-domain. J. Mol. Biol. 292, 1-9 (1999).
14. Legge, G. B. et al. NMR solution structure of the inserted domain of human leukocyte function associated antigen-1. J. Mol. Biol. 295, 1251-1264 (2000).
15. Alonso, J. L., Essafi, M., Xiong, J. P., Stehle, T. & Arnaout, M. A. Does the integrin aA domain act as a ligand for its bA domain? Curr. Biol. 12, R340-R342 (2002).
16. Yang, W., Shimaoka, M., Salas, A., Takagi, J. & Springer, T. A. Inter-subunit signal transmission in integrins by a receptor-like interaction with a pull spring. Proc. Natl. Acad. Sci. USA 101, 2906-2911 (2004).
17. Shimaoka, M. et al. Stabilizing the integrin aM inserted domain in alternative conformations with a range of engineered disulfide bonds. Proc. Natl. Acad. Sci. USA 99, 16737-16741 (2002).
18. Xiong, J.-P., Li, R., Essafi, M., Stehle, T. & Arnaout, M. A. An isoleucine-based allosteric switch controls affinity and shape shifting in integrin CD11b A-domain. J. Biol. Chem. 275, 38762-38767 (2000).
19. Shimaoka, M. et al. Computational design of an integrin I domain stabilized in the open, high affinity conformation. Nat. Struct. Biol. 7, 674-678 (2000).
20. Takahashi, T. T., Austin, R. J. & Roberts, R. W. mRNA display: ligand discovery, interaction analysis and beyond. Trends Biochem Sci 28, 159-165 (2003).
21. Hanes, J. & Pluckthun, A. In vitro selection and evolution of functional proteins by using ribosome display. Proc Natl Acad Sci USA 94, 4937-4942 (1997).
22. Smith, G. P. Filamentous fusion phage: novel expression vectors that display cloned antigens on the virion surface. Science 228, 1315-1317 (1985).
23. Granziero, L., Nelboeck, P., Bedoucha, M., Lanzavecchia, A. & Reid, H. H. Baculovirus cDNA libraries for expression cloning of genes encoding cell-surface antigens. J Immunol Methods 203, 131-139 (1997).
24. Boder, E. T. & Wittrup, K. D. Yeast surface display for screening combinatorial polypeptide libraries. Nat. Biotechnol. 15, 553-557 (1997).
25. Kim, Y. S., Jung, H. C. & Pan, J. G. Bacterial cell surface display of an enzyme library for selective screening of improved cellulase variants. Appl Environ Microbiol 66, 788-793 (2000).
26. Boder, E. T. & Wittrup, K. D. Yeast surface display for directed evolution of protein expression, affinity, and stability. Methods Enzymol. 328, 430-444 (2000).
27. Kieke, M. C., Cho, B. K., Boder, E. T., Kranz, D. M. & Wittrup, K. D. Isolation of anti-T cell receptor scFv mutants by yeast surface display. Protein Eng 10, 1303-1310 (1997).
28. Johns, T. G. et al. Identification of the epitope for the epidermal growth factor receptor-specific monoclonal antibody 806 reveals that it preferentially recognizes an untethered form of the receptor. J Biol Chem 279, 30375-30384 (2004).
29. Bhatia, S. K., Swers, J. S., Camphausen, R. T., Wittrup, K. D. & Hammer, D. A. Rolling adhesion kinematics of yeast engineered to express selectins. Biotechnol. Prog. 19, 1033-1037 (2003).
30. Schweickhardt, R. L., Jiang, X., Garone, L. M. & Brondyk, W. H. Structure-expression relationship of tumor necrosis factor receptor mutants that increase expression. J Biol Chem 278, 28961-28967 (2003).
31. Colby, D. W. et al. Engineering antibody affinity by yeast surface display. Methods Enzymol 388, 348-358 (2004).
32. Lu, C., Shimaoka, M., Salas, A. & Springer, T. A. The binding sites for competitive antagonistic, allosteric antagonistic, and agonistic antibodies to the I domain of integrin LFA-1. J. Immunol. 173, 3972-3978 (2004).
33. Song, G. et al. An atomic resolution view of ICAM recognition in a complex between the binding domains of ICAM-3 and integrin aLb2. Proceed. Natl. Acad. Sci. USA 102, 3366-3371 (2005).
34. Lee, B. & Richards, F. M. The interpretation of protein structures: estimation of static accessibility. J. Mol. Biol. 55, 379-400. (1971).
35. Zhou, H. X. & Shan, Y. Prediction of protein interaction sites from sequence profile and residue neighbor list. Proteins 44, 336-343 (2001).
36. Weetall, M. et al. A homogeneous fluorometric assay for measuring cell adhesion to immobilized ligand using V-well microtiter plates. Anal. Biochem. 293, 277-287 (2001).
37. Kim, M., Carman, C. V. & Springer, T. A. Bidirectional transmembrane signaling by cytoplasmic domain separation in integrins. Science 301, 1720-1725 (2003).
38. Carman, C. V. & Springer, T. A. A transmigratory cup in leukocyte diapedesis both through individual vascular endothelial cells and between them. J. Cell Biol. 167, 377-388 (2004).
39. Rothlein, R. & Springer, T. A. The requirement for lymphocyte function-associated antigen 1 in homotypic leukocyte adhesion stimulated by phorbol ester. J. Exp. Med. 163, 1132-1149 (1986).

40. Rothlein, R., Dustin, M. L., Marlin, S. D. & Springer, T. A. A human intercellular adhesion molecule (ICAM-1) distinct from LFA-1. J. Immunol. 137, 1270-1274 (1986).
41. Hildreth, J. E. K., Gotch, F. M., Hildreth, P. D. K. & McMichael, A. J. A human lymphocyte-associated antigen involved in cell-mediated lympholysis. Eur. J. Immunol. 13, 202-208 (1983).
42. Emsley, J., Knight, C. G., Farmdale, R. W., Barnes, M. J. & Liddington, R. C. Structural basis of collagen recognition by integrin a2b1. Cell 101, 47-56 (2000).
43. Fersht, A. Enzyme Structure and Mechanism, Edn. 2. (W.H. Freeman and Company, New York; 1985).
44. Branden, C. & Tooze, J. Introduction to Protein Structure. (Garland Publishing, Inc., New York and London; 1991).
45. MacArthur, M. W. & Thornton, J. M. Influence of proline residues on protein conformation. J. Mol. Biol. 218, 397-412 (1991).
46. Marvin, J. S. & Hellinga, H. W. Manipulation of ligand binding affinity by exploitation of conformational coupling. Nat. Struct. Biol. 8, 795-798. (2001).
47. Lowman, H., Cunningham, B. & Wells, J. Kinetics of Receptor Binding by hGH Variants From Monovalent Phage Display. Biochemistry 30, 10832-10838 (1991).
48. Rao, B. M., Driver, I., Lauffenburger, D. A. & Wittrup, K. D. Interleukin 2 (IL-2) variants engineered for increased IL-2 receptor alpha-subunit affinity exhibit increased potency arising from a cell surface ligand reservoir effect. Mol Pharmacol 66, 864-869 (2004).
49. Harlan, J. M., Winn, R. K., Vedder, N. B., Doerschuk, C. M. & Rice, C. L. in Adhesion: Its Role in Inflammatory Disease. (eds. J. R. Harlan & D. Liu) 117-150 (W.H. Freeman & Company, New York; 1992).
50. DeLano, W. L. (2004). PyMol, DeLano Scientific, San Carlos, Calif.
51. Demos, S. M., Alkan-Onyuksel, H., Kane, B. J., Ramani, K., Nagaraj, A., greene, R., Klegerman, M., McPherson D D. In vivo targeting of acoustically reflective liposomes for intravascular and transvascular ultrasonic enhancement. J. Am. Coll. Cardiol. 333:867-75 (1999)
52. Sipkins D. A., Gijbels, K., Tropper, F. D., Bednarski, M., Li, K. C., Steinman, L. ICAM-1 expression in autoimmune encephalitis visualized using magnetic resonance imaging. J. Neuroimmunol. 104:1-9 (2000)

The invention claimed is:

1. An isolated polypeptide capable of binding to ICAM-1, comprising an integrin αL I domain, wherein the integrin αL domain has a substituted F265S residue, wherein the substituted polypeptide binds ICAM-1 at a higher affinity than wild type integrin αL protein, wherein the numbering of amino acid residues is in reference to the amino acid sequence of SEQ ID NO: 1 and wherein residue 1 with regards to the isolated substituted polypeptide corresponds to the amino acid residue 26 in SEQ ID NO: 1.

2. An isolated polypeptide capable of binding to ICAM-1, comprising an integrin αL I domain, wherein the integrin αL I domain has substituted residues F265S and F292A, wherein the substituted polypeptide binds ICAM-1 at a higher affinity than wild type integrin αL protein, wherein the numbering of amino acid residues is in reference to the amino acid sequence of SEQ ID NO: 1 and wherein residue 1 with regards to the isolated substituted polypeptide corresponds to the amino acid residue 26 in SEQ ID NO: 1.

3. An isolated polypeptide capable of binding to ICAM-1, comprising an integrin αL I domain, wherein the integrin αL I domain has substituted residues F265S and F292G, wherein the substituted polypeptide binds ICAM-1 at a higher affinity than wild type integrin αL protein, wherein the numbering of amino acid residues is in reference to the amino acid sequence of SEQ ID NO: 1 and wherein residue 1 with regards to the isolated substituted polypeptide corresponds to the amino acid residue 26 in SEQ ID NO: 1.

4. A composition comprising the polypeptide of claim 1 and a pharmaceutically acceptable carrier.

5. A composition comprising the polypeptide of claim 2 and a pharmaceutically acceptable carrier.

6. A composition comprising the polypeptide of claim 3 and a pharmaceutically acceptable carrier.

* * * * *